United States Patent
Koenemann et al.

(10) Patent No.: US 10,125,143 B2
(45) Date of Patent: Nov. 13, 2018

(54) CYANATED BENZOXANTHENE AND BENZOTHIOXANTHENE COMPOUNDS

(71) Applicant: BASF SE, Ludwigshafen (DE)

(72) Inventors: Martin Koenemann, Mannheim (DE); Gerhard Wagenblast, Wachenheim (DE); Sorin Ivanovici, Heidelberg (DE); Gabriele Mattern, Schifferstadt (DE); Martina Mitgude, Gruenstadt (DE); Gerd Weber, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/561,218

(22) PCT Filed: Mar. 24, 2016

(86) PCT No.: PCT/EP2016/056488
§ 371 (c)(1),
(2) Date: Sep. 25, 2017

(87) PCT Pub. No.: WO2016/151068
PCT Pub. Date: Sep. 29, 2016

(65) Prior Publication Data
US 2018/0065980 A1  Mar. 8, 2018

(30) Foreign Application Priority Data

Mar. 26, 2015 (EP) .................................. 15161081

(51) Int. Cl.
| | | |
|---|---|---|
| C07D 491/08 | (2006.01) |
| H01L 51/00 | (2006.01) |
| C07D 493/06 | (2006.01) |
| C09B 5/62 | (2006.01) |
| C09K 11/06 | (2006.01) |
| C09B 57/08 | (2006.01) |
| H01L 33/50 | (2010.01) |
| C07D 491/06 | (2006.01) |
| C07D 491/16 | (2006.01) |
| C07D 495/06 | (2006.01) |
| H01L 51/52 | (2006.01) |

(52) U.S. Cl.
CPC ......... *C07D 493/06* (2013.01); *C07D 491/06* (2013.01); *C07D 491/16* (2013.01); *C07D 495/06* (2013.01); *C09B 5/62* (2013.01); *C09B 57/08* (2013.01); *C09K 11/06* (2013.01); *H01L 33/502* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1088* (2013.01); *C09K 2211/1092* (2013.01); *H01L 51/5281* (2013.01); *H05K 999/99* (2013.01); *Y02E 10/52* (2013.01)

(58) Field of Classification Search
CPC ...... C07D 491/08; H01L 27/322; H01L 51/00
USPC .................... 546/47; 313/501, 504
See application file for complete search history.

(56) References Cited

U.S. PATENT DOCUMENTS

| | | |
|---|---|---|
| 3,748,330 A | 7/1973 | Fuchs et al. |
| 3,808,215 A | 4/1974 | Christmann et al. |
| | (Continued) | |

FOREIGN PATENT DOCUMENTS

| | | |
|---|---|---|
| CN | 103665932 A | 3/2014 |
| DE | 23 28 727 A1 | 1/1975 |
| | (Continued) | |

OTHER PUBLICATIONS

International Search Report dated Jun. 2, 2016 in PCT/EP2016/056488 filed Mar. 24, 2016.
Extended European Search Report dated Sep. 1, 2015 in European Application 15161081.3 filed Mar. 26, 2015.
Tsuguo Yamaoka et al., "N-Phenylglycine-(Thio)xanthene Dye Photoinitiating System and Application to Photopolymer for Visible Laser Exposure," Journal of Applied Polymer Science, Oct. 5, 1989, vol. 38, No. 7, pp. 1271-1285, XP055208873.
A.M. Kadhim et al., "A new intramolecular cyclisation reaction-I: Novel synthesis of Benzo(k, 1)thioxanthene-3,4-dicarboxylic anhydride and derived dyestuffs," Tetrahedron, Jan. 1974, vol. 30, No. 14, pp. 2245-2249, XP055208876.

(Continued)

*Primary Examiner* — Charanjit Aulakh
(74) *Attorney, Agent, or Firm* — Oblon, McClelland, Maier & Neustadt, L.L.P.

(57) ABSTRACT

Disclosed herein are cyanated compounds of the formula (I) wherein at least one of the radicals $R^2$, $R^3$, $R^4$ and $R^5$ is CN, and the remaining radicals are selected from hydrogen, chlorine and bromine; X is O, S, SO or $SO_2$; m is 0, 1, 2, 3 or 4; $R^1$ is selected from bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, etc.; A is a diradical selected from diradicals of the general formulae (A.1), (A.2), (A.3), and (A.4) wherein $R^6$, $(R^7)_n$, $(R^8)_o$ and $(R^9)_p$ are as defined in the claims and in the description. Also disclosed are color converters containing at least one polymer as a matrix material and at least one cyanated compound of formula (I) or mixtures thereof as a fluorescent dye, the use of the color converters, and lighting devices containing an LED and at least one color converter.

16 Claims, No Drawings

(56) References Cited

U.S. PATENT DOCUMENTS

| | | | |
|---|---|---|---|
| 3,812,051 A | 5/1974 | Merkle et al. | |
| 4,939,069 A | 7/1990 | Kawabata et al. | |
| 7,311,858 B2 | 12/2007 | Wang et al. | |
| 7,755,276 B2 | 7/2010 | Wang et al. | |
| 7,906,041 B2 | 3/2011 | Li et al. | |
| 8,274,215 B2 | 9/2012 | Lin et al. | |
| 2004/0062699 A1 | 4/2004 | Oshio | |
| 2011/0068328 A1 | 3/2011 | Koenemann et al. | |
| 2013/0334546 A1 | 12/2013 | Wagenblast et al. | |
| 2014/0076397 A1 | 3/2014 | Wagenblast et al. | |
| 2016/0017219 A1 | 1/2016 | Lub et al. | |
| 2016/0084477 A1 | 3/2016 | Wagenblast et al. | |

FOREIGN PATENT DOCUMENTS

| | | | |
|---|---|---|---|
| DE | 0 004 655 B1 | 3/1982 | |
| EP | 0 315 988 A2 | 5/1989 | |
| FR | 2.089.618 A5 | 1/1972 | |
| FR | 2.130.667 A1 | 11/1972 | |
| FR | 2.194.827 A | 3/1974 | |
| GB | 1 440 450 A | 6/1976 | |
| JP | 2003-217857 A * | 7/2003 | ............. H05B 33/14 |
| JP | 2004-227825 A | 8/2004 | |
| KR | 10-2014-0147037 A | 12/2014 | |
| WO | 2004/029028 A2 | 4/2004 | |
| WO | 2007/006717 A1 | 1/2007 | |
| WO | 2012/010244 A1 | 1/2012 | |
| WO | 2012/113884 A1 | 8/2012 | |
| WO | 2012/152812 A1 | 11/2012 | |
| WO | 2014/131628 A1 | 9/2014 | |
| WO | 2015/019270 A1 | 2/2015 | |
| WO | 2015/062916 A1 | 5/2015 | |

OTHER PUBLICATIONS

Mei-Jin Lin et al., "Bay-substituted perylene bisimide dye with an undistorted planar scaffold and outstanding solid state fluorescence properties," Chemical Communications, Jan. 2012, vol. 48, No. 99, 4 total pages, XP055205899.
U.S. Appl. No. 14/910,078, filed Feb. 4, 2016, US 2016-0177177 A1, Martin Koenemann et al.
U.S. Appl. No. 15/309,631, filed Nov. 8, 2016, US 2017-0183295 A1, Martin Koenemann et al.
U.S. Appl. No. 14/963,713, filed Dec. 9, 2015, US 2016-0084477 A1, Gerhard Wagenblast et al.
U.S. Appl. No. 15/180,161, filed Jun. 13, 2016, US 2016-0284947 A1, Martin Koenemann et al.

* cited by examiner

CYANATED BENZOXANTHENE AND BENZOTHIOXANTHENE COMPOUNDS

The present invention relates to novel cyanated benzoxanthene compounds and cyanated benzothioxanthene compounds and derivatives thereof, to an intermediate compound for preparing them and to a novel process for their preparation of intermediate compounds. The present invention also relates to the use of the cyanated compounds as organic luminescent material, in particular as fluorescent dye in color converters comprising at least one polymer as a matrix material. The present invention also relates to the use of these color converters and to lighting devices comprising at least one LED and at least one color converter.

LEDs (light-emitting diodes, LEDs) are an important class of devices that convert electric energy to light. Because of their low energy consumption, LEDs are increasingly being used as a light source for general lighting, for example in offices and residences, or for architectural lighting, in information signs, small appliances, and in the automobile and aircraft industries. Light emission is based on the recombination of electron-hole pairs (excitons) in the junction region of a pn junction poled in forward direction in a semiconductor. The size of the band gap of this semiconductor determines the approximate wavelength of the light emitted. In order to generate a particular color, LEDs with different band gaps can be combined to form a multi-LED.

Alternatively, a radiation converting luminophore (also referred to as phosphor, or fluorescent colorant or fluorescent dye) can also be combined with a LED. In this context, the radiation emitted by the LED is partly absorbed by the radiation converting luminophore, which is thus induced to photoluminesce. The resulting light color of the LED results from the proportion of LED light transmitted and the emission spectrum of the radiation converting luminophore. According to one approach called "phosphor on a chip", a polymeric material comprising a radiation conversion luminophore is directly applied to the LED light source (LED chip). The polymeric material is applied to the LED chip, for instance, in droplet form or in hemispherical form, as a result of which particular optical effects contribute to the emission of the light. In phosphor on a chip LEDs, the radiation converting luminophores used are generally inorganic materials. Organic luminophore materials are not suitable, because the polymeric material and the radiation converting luminophore are subject to relatively high thermal stress and radiation stress.

In another approach called "remote phosphor", the color converter (also referred to as "converter" or "light converter"), which generally comprises a polymer layer and one or more radiation converting luminophore(s), is spatially separated from the LED source.

The spatial separation between the primary light source, the LED, and the color converter reduces the stress resulting from heat and radiation to such an extent that organic fluorescent dyes can also be used as radiation converting luminophores. Furthermore, LEDs according to the "remote phosphor" concept are more energy-efficient than those according to the "phosphor on a chip" concept. The use of organic fluorescent dyes in these converters offers various advantages, e.g., the hue of the light has good adjustability with fluorescent dyes. Therefore, light with a high color rendering index can be produced.

White light-emitting LEDs are used in a wide range of applications as a light source or as a backlight in full-color displays including in flat panel display applications due to their long lifetime, high reliability and low power consumption. Two methods are commonly used to create white light with LEDs. The basis for the emission of white light is always the superposition (mixing) of various colors. The first approach is through the combination of so called multi-LEDs, usually red, green, and blue ones. Because of the different brightnesses and operating conditions for the various light-emitting diodes, the multi-LED is technically complex and therefore expensive. Moreover, component miniaturization of the multi-LED is severely limited.

The second approach is through the combination of a blue LED with an converter material (phosphor) through luminescence conversion. A conventional converter material is an inorganic converter material such as cerium-doped yttrium aluminum garnet (also referred to as Ce:YAG). A standard Ce:YAG-based white LED emits cool-white light, because the red component in the spectrum is too weak. Therefore, the standard Ce:YAG-based white LED is often unsuitable for many applications in terms of the high color temperature and the low color rendering index of the generated white light. Therefore, the standard Ce:YAG-based white LED is often unsuitable for many applications in terms of the high color temperature and the low color rendering index of the generated white light.

In place of conventional inorganic phosphors, organic phosphors, namely organic fluorescent dyes, can also be used. Organic fluorescent dyes are advantageous in that they allow to create a warm-white light LED light because the fluorescent dyes allows to tailor the hue of the light. In order to achieve white light of a defined color correlation temperature, it may be necessary to use a combination of a green/yellow emitting phosphor and red phosphor. In addition, organic fluorescent dyes are low cost and no costly materials such as rare-earth metals are needed. Although a great variety of organic fluorescent dyes have been available, they often exhibit low quantum yields in a polymer matrix and/or unsufficient photostabilities. If the phosphor shows an efficacy loss over the operational lifetime, for example due to degradation, the color point of the light moves away from the black body locus, i.e. the color point shifts. Therefore, there is an ongoing need for organic phoshors having high quantum yields in the polymer matrix and excellent photostabilities under the practical irradiation conditions. In addition, there is a need for warm-white light generated by the LED.

WO 2015/019270 describes cyanated naphthalenebenzimidazole compounds and their use as fluorescent dye, in particular in color converters for blue LEDs.

WO 2014/131628 describes lighting devices comprising (i) a blue LED as light source and (ii) a color converter comprising a polymer matrix and as organic luminescent material a non-cyanated benzoxanthene or benzothioxanthene compound.

U.S. Pat. No. 3,812,051 describes benzoxanthene and benzothioxanthene compounds as daylight fluorescent pigments.

U.S. Pat. No. 3,748,330 describes benzoxanthene and benzothioxanthene compounds as dyestuffs.

GB 1,440,450 relates to benzothioxanthene compounds as dye for synthetic fibrous material.

WO 2015/062916 describes green/yellow emitting phosphors based on non-cyanated benzimidazoxanthenoisoquinoline for LED lightning.

DE 2328727 describes benzimidazoxanthenoisoquinoline compounds as dyes. The dyes are suitable for cellulose acetate, polyester, or polyamide textiles, articles made from polystyrene, polymethyl methacrylate, PVC, polycarbonates, polyethylene, polypropylene and superpolyamides, and for the production of pigments for lacquers or printing pastes.

EP 0 315 988 relates to a photopolymerizable composition comprising a specific sensitizer and a radical forming agent. A suitable sensitizer is e.g. the following compounds

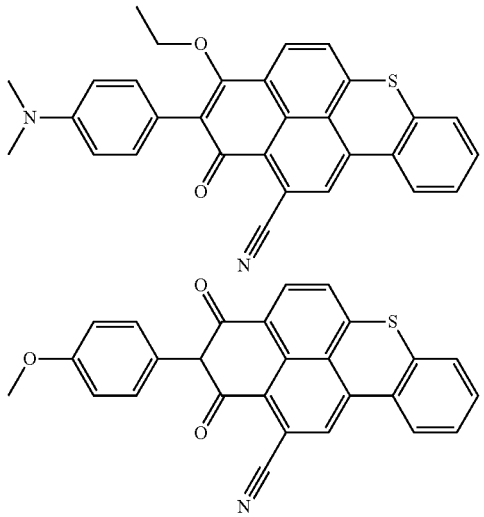

EP 0 004 655 relates to the use of benz(thi)oxanthene compounds for light intensification. None of the concretely disclosed compounds bears a cyano group.

Tsuguo Yamaoka et al describe in Journal of Applied Polymer Science, vol. 38, 1271-1285 (1989) a N-phenyl-glycine-(thio)xanthene dye photoinitiating system exhibiting high initiating efficiency on irradiation.

JP 2004227825 relates to a dye-sensitized photoelectric conversion element, wherein the dye is a benzoxanthene compound.

However, these documents do not describe compounds having the characteristic cyano substituent as claimed in the present invention.

It is therefore an object of the present invention to provide organic fluorescent dyes for combination with a light source, in particular a blue LED light source. The organic fluorescent dye in the polymer matrix shall have an absorption maximum at the peak emission wavelength of the blue light source and to emit in the green and/or yellow range of the electromagnetic spectrum with high quantum yields as well as to have a high stability, especially high photostability under practical irradiation conditions. A further object of the present invention is to provide a white-light emitting LED with high color rendering index and high efficiency through combining a blue LED with green and/or yellow and red luminescent dyes embedded in a polymer matrix, the green and/or yellow luminescent dye having long lifetime under practical irradiation conditions. A further object of the present invention is to provide a white-light emitting LED which allows white light in different color temperatures. Moreover, it is a high need for a process for preparing the compounds of formula (I), which can be performed on large scale and in high yield.

SUMMARY OF THE INVENTION

Therefore, a first aspect of the invention relates to cyanated compounds of the formula (I)

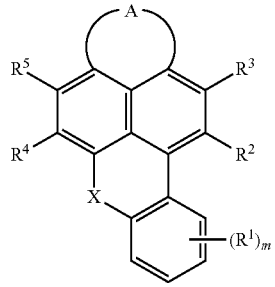

wherein
m is 0, 1, 2, 3 or 4;
each $R^1$ independently from each other is selected from bromine, chlorine, cyano, $NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^c$;
at least one of the radicals $R^2$, $R^3$, $R^4$ and $R^5$ is CN, and the remaining radicals, independently from each other, are selected from hydrogen, chlorine and bromine;
X is O, S, SO or $SO_2$;
A is a diradical selected from diradicals of the general formulae (A.1), (A.2), (A.3), and (A.4)

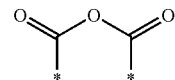

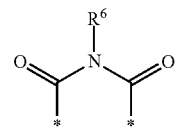

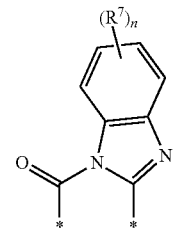

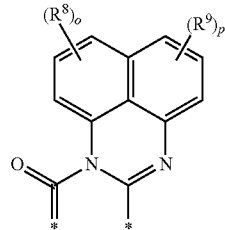

wherein
* in each case denotes the point of attachments to the remainder of the molecule;
n is 0, 1, 2, 3, or 4;
o is 0, 1, 2, or 3;
p is 0, 1, 2, or 3;
R$^6$ is hydrogen, C$_1$-C$_{24}$-alkyl, C$_1$-C$_{24}$-haloalkyl, C$_3$-C$_{24}$-cycloalkyl, C$_6$-C$_{24}$-aryl or C$_6$-C$_{24}$-aryl-C$_1$-C$_{10}$-alkylene, where the rings of cycloalkyl, aryl, and -arylalkylene in the three last-mentioned radicals are unsubstituted or substituted with 1, 2, 3, 4 or 5 identical or different radicals R$^{6a}$, and where C$_1$-C$_{24}$-alkyl, C$_1$-C$_{24}$-haloalkyl and the alkylene moiety of C$_6$-C$_{24}$-aryl-C$_1$-C$_{10}$-alkylene may be interrupted by one or more heteroatoms or heteroatomic groups selected from O, S and NR$^c$;

each R$^7$ independently from each other is selected from bromine, chlorine, cyano, NR$^a$R$^b$, C$_1$-C$_{24}$-alkyl, C$_1$-C$_{24}$-haloalkyl, C$_1$-C$_{24}$-alkoxy, C$_1$-C$_{24}$-haloalkoxy, C$_3$-C$_{24}$-cycloalkyl, heterocycloalkyl, heteroaryl, C$_6$-C$_{24}$-aryl, C$_6$-C$_{24}$-aryloxy, C$_6$-C$_{24}$-aryl-C$_1$-C$_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals R$^{7a}$ and where C$_1$-C$_{24}$-alkyl, C$_1$-C$_{24}$-haloalkyl, C$_1$-C$_{24}$-alkoxy, C$_1$-C$_{24}$-haloalkoxy, and the alkylene moiety of C$_6$-C$_{24}$-aryl-C$_1$-C$_{10}$-alkylene may be interrupted by one or more groups selected from O, S and NR$^c$;

each R$^8$ independently from each other is selected from bromine, chlorine, cyano, NR$^a$R$^b$, C$_1$-C$_{24}$-alkyl, C$_1$-C$_{24}$-haloalkyl, C$_1$-C$_{24}$-alkoxy, C$_1$-C$_{24}$-haloalkoxy, C$_3$-C$_{24}$-cycloalkyl, heterocycloalkyl, heteroaryl, C$_6$-C$_{24}$-aryl, C$_6$-C$_{24}$-aryloxy, C$_6$-C$_{24}$-aryl-C$_1$-C$_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals R$^{8a}$ and where C$_1$-C$_{24}$-alkyl, C$_1$-C$_{24}$-haloalkyl, C$_1$-C$_{24}$-alkoxy, C$_1$-C$_{24}$-haloalkoxy, and the alkylene moiety of C$_6$-C$_{24}$-aryl-C$_1$-C$_{10}$-alkylene may be interrupted by one or more groups selected from O, S and NR$^c$;

each R$^9$ independently from each other is selected from bromine, chlorine, cyano, NR$^a$R$^b$, C$_1$-C$_{24}$-alkyl, C$_1$-C$_{24}$-haloalkyl, C$_1$-C$_{24}$-alkoxy, C$_1$-C$_{24}$-haloalkoxy, C$_3$-C$_{24}$-cycloalkyl, heterocycloalkyl, heteroaryl, C$_6$-C$_{24}$-aryl, C$_6$-C$_{24}$-aryloxy, C$_6$-C$_{24}$-aryl-C$_1$-C$_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals R$^{9a}$ and where C$_1$-C$_{24}$-alkyl, C$_1$-C$_{24}$-haloalkyl, C$_1$-C$_{24}$-alkoxy, C$_1$-C$_{24}$-haloalkoxy, and the alkylene moiety of C$_6$-C$_{24}$-aryl-C$_1$-C$_{10}$-alkylene may be interrupted by one or more groups selected from O, S and NR$^c$;

R$^{1a}$, R$^{6a}$, R$^{7a}$, R$^{8a}$, R$^{9a}$ are independently of one another selected from C$_1$-C$_{24}$-alkyl, C$_1$-C$_{24}$-fluoroalkyl, C$_1$-C$_{24}$-alkoxy, fluorine, chlorine and bromine;

R$^a$, R$^b$, R$^c$ are independently of one another are selected from hydrogen, C$_1$-C$_{20}$-alkyl, C$_3$-C$_{24}$-cycloalkyl, heterocycloalkyl, hetaryl and C$_6$-C$_{24}$-aryl.

The compounds of formula (I) of the present invention are characterized by the cyano group(s) attached to the core of the molecule. They are characterized by light emission in the yellow/green spectral range, making them particularly suitable for applications in white LEDs. Additionally, they exhibit high fluorescence quantum yields. The cyano group(s) significantly improve(s) the stability and life time of the inventive compounds under practical irradiation conditions. Thus, the invention is especially advantageous for providing compounds for use in color converters for conversion of light which has been generated by a LED, especially a blue LED or a white LED.

In a second aspect, the present invention relates to a color converter comprising at least one polymer as a matrix and at least one cyanated compound of the formula I or a mixture of these as defined above as a fluorescent dye, wherein the at least one polymer consists essentially of polystyrene, polycarbonate, polymethylmethacrylate, polyvinylpyrrolidone, polymethacrylate, polyvinyl acetate, polyvinyl chloride, polybutene, silicone, polyacrylate, epoxy resin, polyvinyl alcohol, poly(ethylene vinylalcohol)-copolymer (EVA, EVOH), polyacrylonitrile, polyvinylidene chloride (PVDC), polystyreneacrylonitrile (SAN), polybutylene terephthalate (PBT), polyethylene terephthalate (PET), polyvinyl butyrate (PVB), polyvinyl chloride (PVC), polyamides, polyoxymethylenes, polyimides, polyetherimides or mixtures thereof.

In a third aspect, the present invention relates to the use of a color converter as defined above for conversion of light generated by LEDs.

In a fourth aspect, the present invention relates to a lighting device comprising at least one LED and at least one color converter.

In a fifth aspect, the present invention relates to a device producing electric power upon illumination comprising a photovoltaic cell and the color converter as defined above, where at least a part of the light not absorbed by the photovoltaic cell is absorbed by the color converter.

In a further aspect, the present invention also relates to a compound of the formula (II)

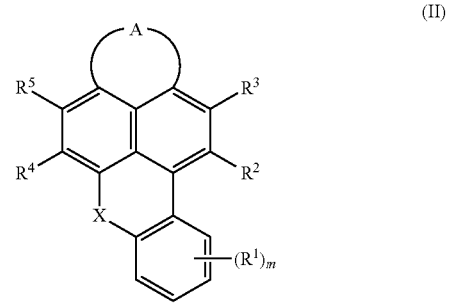

wherein
at least one of the radicals R$^2$, R$^3$, R$^4$ and R$^5$ is selected from bromine and chlorine and the remaining radicals R$^2$, R$^3$, R$^4$ and R$^5$ are hydrogen;
X is S, SO or SO$_2$; and
A and (R$^1$)$_m$ are as defined above; as valuable intermediate compound in the preparation of compounds of formula (I).

Yet, a further aspect of the present invention relates to a process for preparing benzo[k,l]xanthene compounds of formula (III.1)

(III.1)

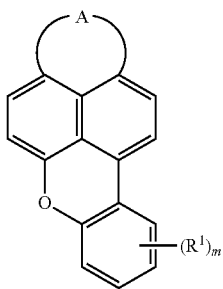

where A is a radical of formulae (A.1), (A.2), (A.3) or (A.4) as defined above; and $(R^1)_m$ is as defined above. The compounds of formula (III.1) are valuable key intermediates in the preparation of compounds of formula (I), where X is O.

Embodiments of the Invention

Specifically, the invention comprises the following preferred embodiments:

1. A cyanated compound of formula I

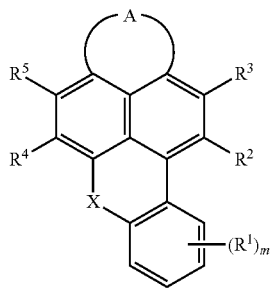

(I)

wherein
m is 0, 1, 2, 3 or 4;
each $R^1$ independently from each other is selected from bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^c$;
at least one of the radicals $R^2$, $R^3$, $R^4$ and $R^5$ is CN, and the remaining radicals, independently from each other, are selected from hydrogen, chlorine and bromine;
X is O, S, SO or $SO_2$;
A is a diradical selected from diradicals of the general formulae (A.1), (A.2), (A.3), and (A.4)

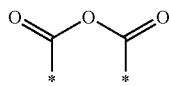

(A.1)

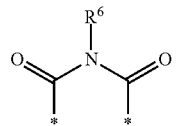

(A.2)

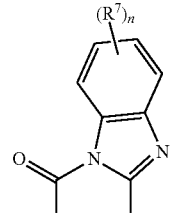

(A.3)

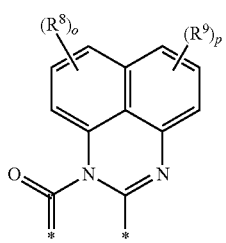

(A.4)

wherein
* in each case denotes the point of attachments to the remainder of the molecule;
n is 0, 1, 2, 3 or 4;
o is 0, 1, 2 or 3;
p is 0, 1, 2 or 3;
$R^6$ is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and aryl-alkylene in the three last-mentioned radicals are unsubstituted or substituted with 1, 2, 3, 4 or 5 identical or different radicals $R^{6a}$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from O, S and $NR^c$;
each $R^7$ independently from each other is selected from bromine, chlorine, cyano, —$NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{7a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^c$;
each $R^8$ independently from each other is selected from bromine, chlorine, cyano, $NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{8a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^c$;

each $R^9$ independently from each other is selected from bromine, chlorine, cyano, $NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{9a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^c$;

$R^{1a}$, $R^{6a}$, $R^{7a}$, $R^{8a}$, $R^{9a}$ are independently of one another selected from $C_1$-$C_{24}$-alkyl, $C_1$-$C_{24}$-fluoroalkyl, $C_1$-$C_{24}$-alkoxy, fluorine, chlorine and bromine;

$R^a$, $R^b$, $R^c$ are independently of one another are selected from hydrogen, $C_1$-$C_{20}$-alkyl, $C_3$-$C_{24}$-cycloalkyl, heterocycloalkyl, hetaryl and $C_6$-$C_{24}$-aryl.

2. The cyanated compound of formula (I) according to embodiment 1, in which X is O or S.

3. The cyanated compound of formula (I) according to embodiment 1 or 2, where $R^2$ and $R^4$ are each cyano and $R^3$ and $R^5$ are each hydrogen.

4. The cyanated compound of formula (I) according to any of the preceding embodiments, wherein A is a radical of the formula (A.2).

5. The cyanated compound of formula (I) according to embodiment 4, wherein $R^6$ is selected from linear $C_1$-$C_{24}$-alkyl, a radical of the formula (B.1) and a radical of the formula (B.2)

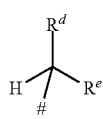
(B.1)

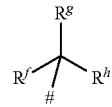
(B.2)

in which
\# represents the bonding site to the nitrogen atom;
$R^d$ and $R^e$, in the formula (B.1), independently from each other are selected from $C_1$-$C_{23}$-alkyl, where the sum of the carbon atoms of the $R^d$ and $R^e$ radicals is an integer from 2 to 23;
$R^f$, $R^g$ and $R^h$, in the formula (B.2) are independently selected from $C_1$- to $C_{20}$-alkyl, where the sum of the carbon atoms of the $R^f$, $R^g$ and $R^h$ radicals is an integer from 3 to 23.

6. The cyanated compound of formula (I) according to embodiment 4, in which $R^6$ is selected from a radical of the formula (C.1), a radical of the formula (C.2) and a radical of the formula (C.3).

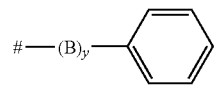
(C.1)

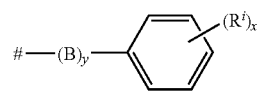
(C.2)

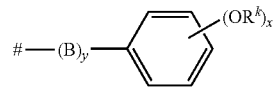
(C.3)

where
\# represents the bonding side to the nitrogen atom,
B where present, is a $C_1$-$C_{10}$-alkylene group which may be interrupted by one or more nonadjacent groups selected from —O— and —S—,
y is 0 or 1,
$R^i$ is independently of one another selected from $C_1$-$C_{24}$-alkyl, $C_1$-$C_{24}$-fluoroalkyl, fluorine, chlorine or bromine,
$R^k$ is independently of one another selected from $C_1$-$C_{24}$-alkyl,
x in formulae C.2 and C.3 is 1, 2, 3, 4 or 5.

7. The cyanated compound of formula (I) according to embodiment 4 which is selected from

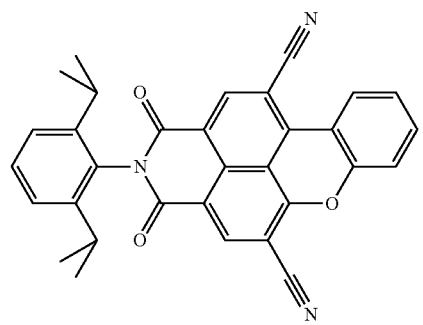

or

-continued
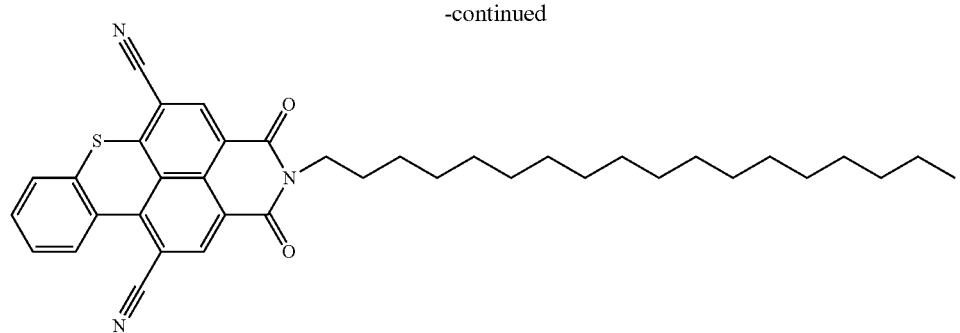
8. The cyanated compound of formula (I) according to embodiment 4 which is selected from
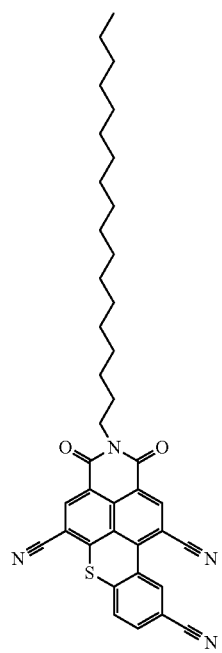
-continued
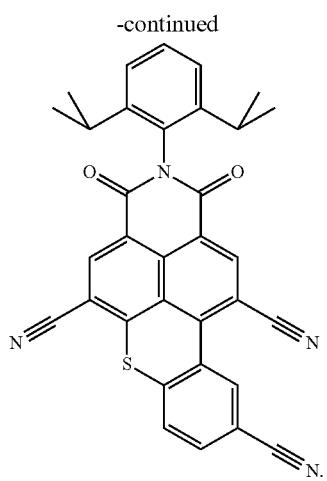
9. The cyanated compound of formula (I) according to any of embodiments 1 to 3, wherein A is a radical of the formula (A.3).
10. The cyanated compound of formula (I) according to embodiment 9 which is
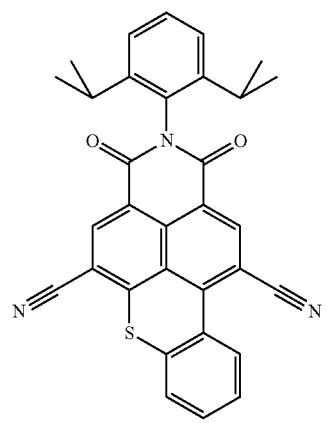
or
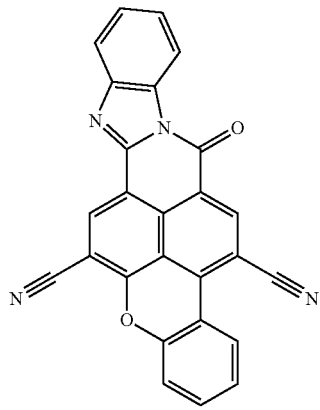
or

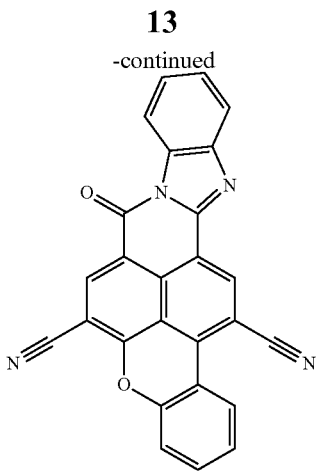

or a mixture thereof.

11. The cyanated compound according to any of the preceding embodiments, wherein m is zero or one.

12. A process for preparing a compound of formula (I)

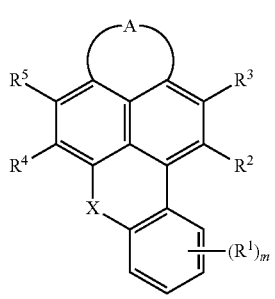

wherein

A is a radical of formulae (A.1), (A.2), (A.3) or (A.4);

X is O, S, S(O) or SO$_2$;

(R$^1$)$_m$, R$^2$, R$^3$, R$^4$, and R$^5$ are as defined above;

comprising:

a) providing a compound of formula (III)

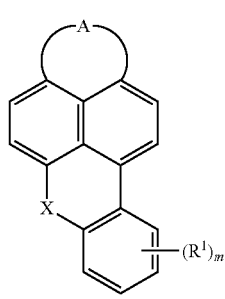

b) reacting the compound of formula (III) with a halogenating agent of formula selected from a brominating agent or a chlorinating agent to give a compound of compound of formula (II)

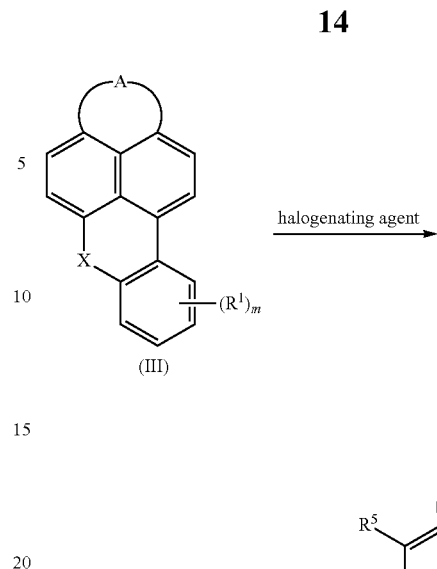

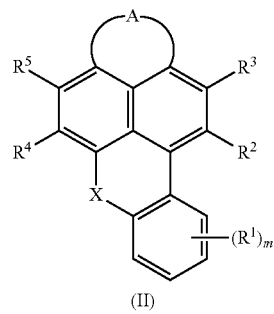

wherein at least one of the radicals R$^2$, R$^3$, R$^4$ and R$^5$ is halogen selected from chlorine or bromine and the remaining radicals are each hydrogen, with the proviso that radicals different from hydrogen have the same meaning;

c) subjecting the compound of the formula (II) obtained in step b) to a substitution of the halogen by cyano to give a compound of formula (I).

13. A color converter comprising at least one polymer as a matrix and at least one cyanated compound of the formula I or a mixture of these as defined in any of the preceding embodiments as a fluorescent dye, wherein the at least one polymer consists essentially of polystyrene, polycarbonate, polymethylmethacrylate, polyvinylpyrrolidone, polymethacrylate, polyvinyl acetate, polyvinyl chloride, polybutene, silicone, polyacrylate, epoxy resin, polyvinyl alcohol, poly (ethylene vinylalcohol)-copolymer (EVA, EVOH), polyacrylonitrile, polyvinylidene chloride (PVDC), polystyreneacrylonitrile (SAN), polybutylene terephthalate (PBT), polyethylene terephthalate (PET), polyvinyl butyrate (PVB), polyvinyl chloride (PVC), polyamides, polyoxymethylenes, polyimides, polyetherimides or mixtures thereof.

14. The color converter according to embodiment 13, wherein the at least one polymer consists essentially of polystyrene, polycarbonate, or polyethylene terephthalate.

15. The color converter according to embodiment 13 or 14, wherein the color converter additionally comprises at least one inorganic white pigment as a scattering body.

16. The color converter according to any of embodiments 13 to 15, comprising at least one further organic fluorescent dye selected from compounds or mixtures of the formulae IV, V and VI

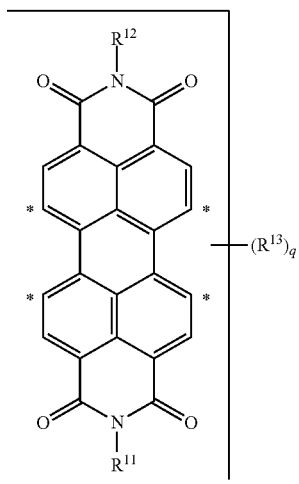

(IV)

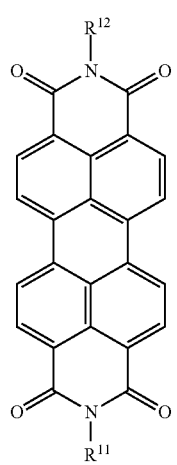

(V)

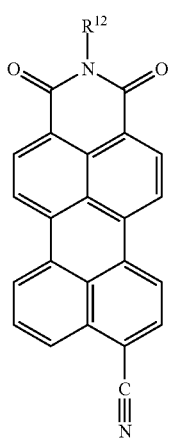

(VI)

in which q is 1 to 4, $R^{11}$, $R^{12}$ are each independently $C_1$-$C_{30}$-alkyl, $C_3$-$C_8$-cycloalkyl, aryl, hetaryl, aryl-$C_1$-$C_{10}$-alkylene, where the aromatic ring in the three latter radicals is unsubstituted or mono- or polysubstituted by $C_1$-$C_{10}$-alkyl, $R^{13}$ is aryloxy which is unsubstituted or mono- or polysubstituted by halogen, $C_1$-$C_{10}$-alkyl or $C_6$-$C_{10}$-aryl, where the $R^{13}$ radicals are at one or more of the positions indicated by *.

17. The color converter according to embodiment 16, wherein the further organic fluorescent dye is selected from N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide, N,N'-bis(2,6-diisopropylphenyl)-1,7-di(p-tert-octylphenoxy)perylene-3,4;9,10-tetracarboximide, N,N'-bis(2,6-diisopropylphenyl)-1,6-di(p-tert-octylphenoxy)perylene-3,4;9,10-tetracarboximide, N,N'-bis(2,6-diisopropylphenyl)-1,7-diphenoxyperylene-3,4;9,10-tetracarboximide, N,N'-bis(2,6-diisopropylphenyl)-1,6-diphenoxyperylene-3,4;9,10-tetracarboximide, N,N'-bis(2,6-diisopropylphenyl)-1,7-di(2,6-diphenyllphenoxy)perylene-3,4;9,10-tetracarboximide, N,N'-bis(2,6-diisopropylphenyl)-1,6-di(2,6-diphenylphenoxy)perylene-3,4;9,10-tetracarboximide and mixtures thereof.

18. The color converter according to embodiment 16, wherein the further organic fluorescent dye is selected from N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide, N,N'-bis(2,6-diisopropylphenyl)-1,7-di(p-tert-octylphenoxy)perylene-3,4;9,10-tetracarboximide, N,N'-bis(2,6-diisopropylphenyl)-1,6-di(p-tert-octylphenoxy)perylene-3,4;9,10-tetracarboximide, N,N'-bis(2,6-diisopropylphenyl)-1,7-diphenoxyperylene-3,4;9,10-tetracarboximide, or N,N'-bis(2,6-diisopropylphenyl)-1,6-diphenoxyperylene-3,4;9,10-tetracarboximide, and mixtures thereof.

19. The use of a color converter as defined in any of embodiments 13 to 18 for conversion of light generated by LEDs.

20. The use of a color converter as defined in embodiment 19 for conversion of light which has been generated by a blue LED.

21. The use of a color converter as defined in embodiment 19 for conversion of light which has been generated by a white LED.

22. The use of a color converter as defined in any of embodiments 13 to 18 in displays.

23. A lighting device comprising at least one LED and at least one color converter according to any of embodiments 13 to 18.

24. The lighting device according to embodiment 23, comprising at least one LED and at least one color converter according to any of embodiments 13 to 18, wherein LED and color converter are in a remote phosphor arrangement.

25. A device producing electric power upon illumination comprising a photovoltaic cell and the color converter as defined in any of embodiments 13 to 18, where at least a part of the light not absorbed by the photovoltaic cell is absorbed by the color converter.

26. A compound of the formula (II)

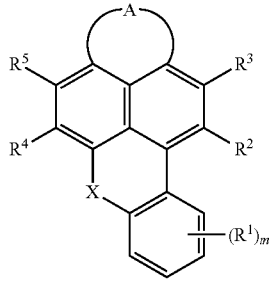
(II)

wherein
at least one of the radicals $R^2$, $R^3$, $R^4$ and $R^5$ is selected from bromine and chlorine and the remaining radicals $R^2$, $R^3$, $R^4$ and $R^5$ are hydrogen;
X is S, SO or $SO_2$;
A is a radical of the general formulae (A.1), (A.2), (A.3), or (A.4) as defined in embodiment 1
$R^1$ is bromine, chlorine, cyano, $-NR^aR^b$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy and aryl-alkylene in the six last-mentioned radicals are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^c$, wherein $R^a$, $R^b$ and $R^c$ are as defined in embodiment 1; and
m is 0, 1, 2, 3 or 4.

27. A process for preparing a benzo[k,l]xanthene compound of formula (III.1)

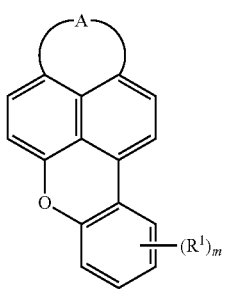
(III.1)

wherein
$(R^1)_m$, is as defined above; and
A is a radical of formulae (A.1), (A.2), (A.3) or (A.4);
comprising reacting a 4,5-dihalogen-naphthalenedicarboxylic acid derivate of formula (VII) with a boronic acid derivative of formula (VIII) in the presence of a base and a transition metal catalyst to give a compound of formula (III.1))

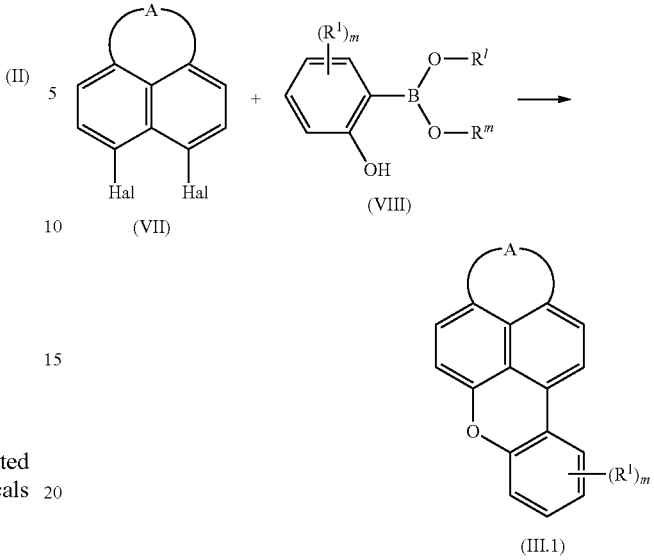

wherein
Hal in each case is chlorine or bromine;
$R^l$ and $R^m$ are each independently hydrogen or $C_1$-$C_4$-alkyl, or $R^l$ and $R^m$ together form an 1,2-ethylene or 1,2-propylene moiety the carbon atoms of which may be unsubstituted or may all or in part be substituted by methyl groups.

DETAILED DESCRIPTION OF INVENTION

If the group A is a radical of the formulae (A.3) or (A.4), the compounds of the formula I may be present as mixtures of two regioisomers with regard to the point of attachment to the naphthalene scaffold. The structures depicted represent both possible combinations of syn or anti position of the carbonyl group of said radical (A.3) and (A.4), respectively, relative to X. The invention provides both the pure regioisomers and the mixtures thereof and the use according to the invention of the pure regioisomers of the compound I or their mixtures.

In the context of the present invention, a "blue LED" is understood to mean an LED which emits light in the blue range of the electromagnetic spectrum, i.e. in the wavelength range from 400 to 500 nm, preferably 420 to 480 nm and especially 440 to 470 nm. Suitable semiconductor materials are silicon carbide, zinc selenide and nitrides such as aluminum nitride (AlN), gallium nitride (GaN), indium nitride (InN) and indium gallium nitride (InGaN). In the context of the present invention, a "green LED" is understood to mean an LED which emits light in the wavelength range from 501 to 560 nm, preferably 501 to 540 nm and especially 520 to 540 nm. Suitable semiconductor materials are for example based on GaInNAs.

In the context of the present invention, a "white LED" is understood to mean an LED which produces white light. Examples of a white LED are multi-LEDs or a blue LED in combination with at least one radiation converting luminophore.

The term "white light" relates to light having a color correlation temperature (CCT) between 2 000 to 20 000 K, especially 2 500 to 20 000 K. The term "blue light" relates to light having a wavelength in the range from 440 to 490 nm. The term "green light" relates to light having a wavelength in the range from 490 to 560 nm. The term "yellow light" relates to light having a wavelength in the range from 560 to 590 nm. The term "orange light" relates to light having a wavelength in the range from 590 to 620 nm. The term "red light" or "pink light" relates to light having a wavelength in the range from 620 to 750 nm.

In the context of the present invention, "color converter" is understood to mean all physical devices capable of absorbing light of particular wavelengths and converting it to light of a second wavelength. Color converters are, for example, part of lighting devices, especially those lighting devices which utilize UV light or LEDs or OLEDs as a light source, or of fluorescence conversion solar cells. Thus, the blue light may be (at least) partly converted into visible light of higher wavelengths than the excitation wavelengths.

The color rendering index (CRI) is understood to mean a photometric parameter which gives an assessment of a light source in comparison to an ideal light source (Planckian radiator) with regard to quality in terms of the color rendering of up to 14 listed reference colors (CIE 1974). The size of the CRI value may be between 0 and 100 and describes the extent to which a light source is able to render the different colors of reference colors. The first commercially available white light LEDs had color rendering indices of 70 to 80. Sunlight has a CRI of up to 100.

The word "essentially" in the context of the present invention encompasses the words "completely", "wholly" and "all". The word encompasses a proportion of 90% or more, such as 95% or more, especially 99% or 100%.

The definitions of the variables specified in the above formulae use collective terms which are generally representative of the respective substituents. The definition $C_n$-$C_m$ gives the number of carbon atoms possible in each case in the respective substituent or substituent moiety.

The expression "halogen" denotes in each case fluorine, bromine, chlorine or iodine, particularly chlorine, bromide or iodine.

In the context of the present invention, the expression "alkyl" comprises straight-chain or branched alkyl groups. Alkyl is preferably $C_1$-$C_{24}$-alkyl, more preferably $C_1$-$C_{20}$-alkyl. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethyl pentyl, n-octyl, 1-methylheptyl, 2-methylheptyl, 1-ethylhexyl, 2-ethylhexyl, 1-propyl pentyl, 2-propylpentyl, n-nonyl, 1-methyloctyl, 2-methyloctyl, 1-ethylheptyl, 2-ethylheptyl, 1-propylhexyl, 2-propylhexyl, 1-butylpentyl, n-decyl, 2-methyldecyl, 1-methylnonyl, 2-methylnonyl, 1-ethyloctyl, 2-ethyloctyl, 1-propylheptyl, 2-propylheptyl, 1-butylhexyl, 2-butylhexyl, n-undecyl, 2-ethylnonyl, 1-propyloctyl, 2-propyloctyl, 1-butylheptyl, 2-butylheptyl, 1-pentylhexyl, n-dodecyl, 2-ethyldecyl, 2-propylnonyl, 1-butyloctyl, 2-butyloctyl, 1-pentylheptyl, 2-pentylheptyl, 2-propyldecyl, n-tridecyl, 1-pentyloctyl, 2-pentyloctyl, 1-hexylheptyl, 2-butylnonyl, n-tetradecyl, 1-hexyloctyl, 2-hexyloctyl, 2-pentylnonyl, 2-hexylnonyl, 2-pentyldecyl, 2-butyldecyl, n-hexadecyl, 1-heptyloctyl, 2-heptylnonyl, 2-hexyldecyl, 2-heptyldecyl, n-octadecyl, 2-octyldecyl, n-eicosyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-methyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl and 2-methyloctacosanyl.

Haloalkyl and all haloalkyl moieties in haloalkoxy: straight-chain or branched alkyl groups having 1 to 24, frequently 1 to 20 carbon atoms (as specified above), where some or all of the hydrogen atoms in these groups are replaced by halogen atoms as specified above.

The expression alkyl also comprises alkyl radicals whose carbon chains may be interrupted by one or more nonadjacent groups which are selected from —O—, —S— and —NR$^c$. R$^c$ is hydrogen, $C_1$-$C_{20}$-alkyl, $C_3$-$C_{24}$-cycloalkyl, heterocycloalkyl, $C_6$-$C_{24}$-aryl or hetaryl. The above remarks regarding alkyl also apply to the alkyl moiety in alkoxy, alkylthio (=alkylsulfanyl), monoalkylamino, dialkylamino and the alkylene moiety in aryl-$C_1$-$C_{10}$-alkylene.

Examples of alkyl groups whose carbon chains are interrupted by one or more, e.g. 1, 2, 3, 4, 5, 6, 7, 8 or more than 8, nonadjacent groups are especially 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetra-oxatetradecyl; 2-methylthioethyl, 2-ethylthioethyl, 2-propylthioethyl, 2-isopropylthio-ethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethyl-thiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-tri-thiadecyl, 3,6,9-trithiaundecyl, 3,6,9-trithiadodecyl, 3,6,9,12-tetrathiatridecyl and 3,6,9,12-tetrathiatetradecyl; 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl; (1-ethylethylidene)aminoethylene, (1-ethylethylidene)aminopropylene, (1-ethylethylidene)aminobutylene, (1-ethylethylidene)aminodecylene and (1-ethylethylidene)aminododecylene.

Alkylene represents a linear or branched saturated hydrocarbon chain having from 1 to 10 and especially from 1 to 6 carbon atoms, such as linear $C_1$-$C_6$-alkylene, e.g. methylene (—$CH_2$—), ethane-1,2-diyl, propane-1,3-diyl, butane-1,4-diyl, pentane-1,5-diyl or hexane-1,6-diyl and branched $C_2$-$C_6$-alkylene, such as ethane-1,1-diyl, propane-1,2-diyl, butane-1,2-diyl or butane-1,3-diyl.

$C_1$-$C_{24}$-alkoxy refers to $C_1$-$C_{24}$-alkyl as defined above, attached via an oxygen atom to the remainder. Examples of alkoxy groups are especially methoxy, ethoxy, propoxy, isopropoxy, butoxy, isobutoxy, sec-butoxy, tert-butoxy, pentoxy, isopentoxy, neopentoxy, tert-pentoxy and hexoxy.

$C_1$-$C_{24}$-haloalkoxy refers to $C_1$-$C_{24}$-haloalkyl as defined above which is bound to the remainder of the molecule via an oxygen atom.

The term $C_3$-$C_{24}$-cycloalkyl refers to a monocyclic or polycyclic, e.g. mono-, bi- or tricyclic, 3- to 30-membered saturated cycloaliphatic radical. Examples of monocyclic rings are cyclopropyl, cyclobutyl, cyclopentyl, cyclohexyl, cycloheptyl or cyclooctyl, especially cyclopentyl and cyclohexyl. Examples of polycyclic rings are perhydroanthracyl, perhydronaphthyl, perhydrofluorenyl, perhydrochrysenyl, perhydropicenyl, adamantyl, bicyclo[1.1.1]pentyl, bicyclo[2.2.1]heptyl, bicyclo[4.2.2]decyl, bicyclo[2.2.2]octyl, bicyclo[3.3.0]octyl bicyclo[3.3.2]decyl, bicyclo[4.4.0]decyl, bicyclo[4.3.2] undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl and the like.

The term heterocycloalkyl refers to nonaromatic, partially unsaturated or fully saturated, heterocyclic rings having generally 5 to 8 ring members, preferably 5 or 6 ring members, comprising besides carbon atoms as ring members, one, two, three or four heteroatoms or heteroatom-containing groups selected from O, N, $NR^c$, S, SO and $S(O)_2$ as ring members, wherein $R^c$ is as defined above. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

The expression $C_6$-$C_{24}$-aryl refers to an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl.

Aryl which bears one or more $C_1$-$C_{24}$-alkyl radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

The term $C_6$-$C_{24}$-aryl-$C_1$-$C_{10}$-alkylene refers to an aromatic radical having 6 to 24 carbon atoms as defined above, which is bound to the remainder of the molecule via a $C_1$-$C_{10}$-alkylene group, as defined above, in particular via a methylene, 1,1-ethylene or 1,2-ethylene group. Examples for $C_6$-$C_{24}$-aryl-$C_1$-$C_{10}$-alkylene are benzyl, 1-phenylethyl and 2-phenylethyl, phenylpropyl, naphthylmethyl, naphthylethyl etc.

$C_6$-$C_{24}$-aryloxy: $C_6$-$C_{24}$-aryl as defined above, which is bonded to the skeleton via an oxygen atom (—O—). Preference is given to phenoxy and naphthyloxy.

The term "hetaryl" (heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2 furyl (furan-2-yl), 3-furyl (furan-3-yl), 2-thienyl (thiophen-2-yl), 3 thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3 isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4 oxadiazol 2 yl, 1,2,4 thiadiazol-3-yl, 1,2,4-thiadiazol-5-yl, 1,3,4-thiadiazol-2-yl, 4H[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3 pyridazinyl, 4-pyridazinyl, 2-pyrimidinyl, 4-pyrimidinyl, 5-pyrimidinyl, 2 pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Embodiments of the present invention as well as preferred compounds of the present invention are outlined in the following paragraphs. The remarks below concerning preferred embodiments of the variables of the compound of the formula (I), especially with regard to the substituents A, X, $(R^1)_m$, $R^2$, $R^3$, $R^4$, $R^5$ are valid both on their own and, in particular, in every possible combination with each other.

When * or # appears in a formula showing a preferred substructure of a compound of the present invention, it denotes the attachment bond to the remainder of the molecule.

Preferred are compounds of the formula (I), wherein X is O. Compounds of formula (I), where X is O are also referred to as compounds of formula (I.1).

Also preferred are compounds of the formula (I), wherein X is S. Compounds of formula (I), where X is S are also referred to as compounds of formula (I.2).

Preferred are compounds of the formula (I), wherein two of the radicals $R^2$, $R^3$, $R^4$ and $R^5$ are cyano and the remaining two radicals $R^2$, $R^3$, $R^4$ and $R^5$ are selected from hydrogen and bromine. Even more preferred are compounds of formula (I), wherein two of the radicals $R^2$, $R^3$, $R^4$ and $R^5$ are cyano and the remaining two radicals $R^2$, $R^3$, $R^4$ and $R^5$ are each hydrogen. In particular, $R^2$ and $R^4$ are each cyano and $R^3$ and $R^5$ are each hydrogen.

Preferred are compounds of the formula (I), wherein m is 0, i.e. $R^1$ is absent.

Preferred are also compounds of the formula (I), wherein m is 1 or 2. In this context, each $R^1$ is preferably selected from cyano, bromine, chlorine, $C_1$-$C_4$-alkyl, $C_1$-$C_4$-alkoxy, $C_1$-$C_4$-haloalkyl, phenyl and phenyloxy, where the phenyl ring in the two last mentioned radicals is unsubstituted or carries 1, 2 or 3 substituents selected from $C_1$-$C_{10}$-alkyl. As examples for $C_1$-$C_4$-alkyl, there may be mentioned methyl, ethyl, n-propyl, isopropyl, n-butyl or isobutyl. As example for $C_1$-$C_4$-alkoxy, there may be mentioned methoxy, ethoxy, n-propoxy, isopropoxy, n-butoxy or isobutoxy. As examples for $C_1$-$C_4$-haloalkyl, in particular $C_1$-$C_2$-haloalkyl may be mentioned. In particular, $R^1$ is selected from cyano, bromine, and phenyl which is unsubstituted or carries 1 or 2 radicals selected from $C_1$-$C_4$-alkyl; especially $R^1$ is cyano. Especially, m is 1. More especially, m is 1 and $R^1$ is cyano.

According to a first group of embodiments, compounds of the formula (I) are preferred, wherein group A is a radical of the formula (A.1). Compounds of the formula (I), where A is a radical of the formula (A.1) are also referred to as compounds of formula (I-A.1),

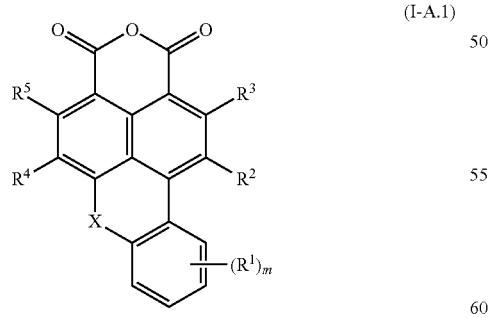

(I-A.1)

wherein
m, X, $R^1$, $R^2$, $R^3$, $R^4$, and $R^5$ are as defined above and especially have one of the preferred meanings.

Examples for preferred inventive compounds of formula (I-A.1) are shown below:

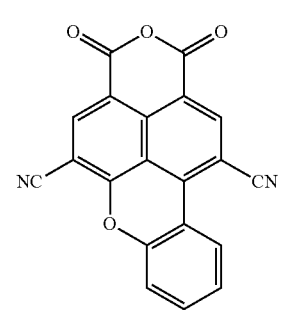

(I-A.1-1)

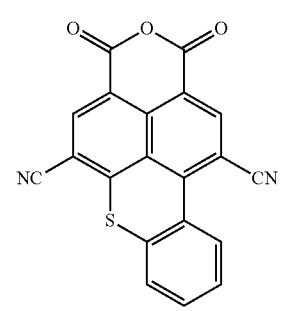

(I-A.1-2)

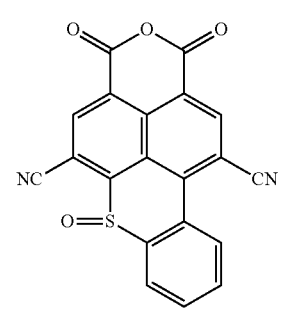

(I-A.1-3)

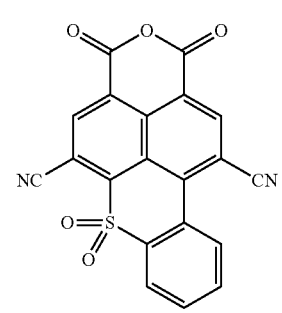

(I-A.1-4)

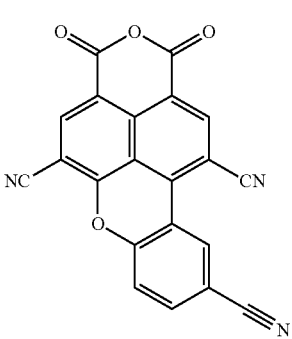

(I-A.1-5)

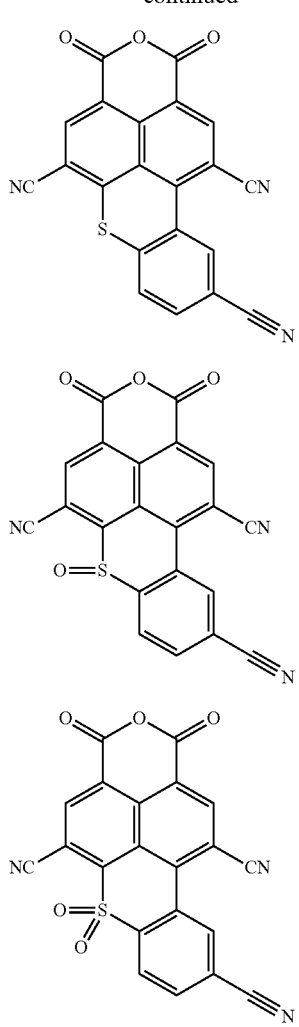

(I-A.1-6)

(I-A.1-7)

(I-A.1-8)

According to a second group of embodiments, compounds of the formula (I) are preferred, wherein A is a radical of the formula (A.2). Compounds of the formula (I), where A is a radical of the formula (A.2) are also referred to as compounds of formula (I-A.2),

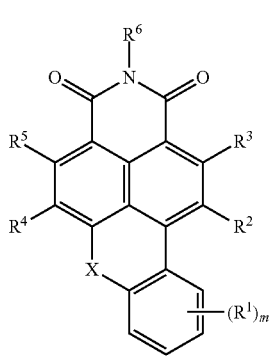

(I-A.2)

wherein
m, X, $R^1$, $R^2$, $R^3$, $R^4$, $R^5$ and $R^6$ are as defined above. In particular, m, X, $R^1$, $R^2$, $R^3$, $R^4$ and $R^5$ have one of the preferred meanings mentioned above.

In the compounds of the formula (I-A.2), $R^6$ is preferably selected from hydrogen, linear $C_1$-$C_{24}$-alkyl, branched $C_3$-$C_{24}$-alkyl, $C_6$-$C_{10}$-aryl and $C_6$-$C_{10}$-aryl-$C_1$-$C_{10}$-alkylene, where the aryl ring in the two last mentioned moieties is unsubstituted or substituted with 1, 2, 3, 4 or 5 identical or different radicals $R^{6a}$. In a special embodiment, $R^6$ is selected from linear $C_1$-$C_{24}$-alkyl, a radical of the formula (B.1) and a radical of the formula (B.2)

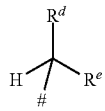

(B.1)

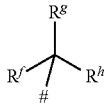

(B.2)

in which
# is the bonding site to the nitrogen atom;
$R^d$ and $R^e$, in the formula (B.1), independently from each other are selected from $C_1$-$C_{23}$-alkyl, where the sum of the carbon atoms of the $R^d$ and $R^e$ radicals is an integer from 2 to 23;
$R^f$, $R^g$ and $R^h$, in the formula (B.2) are independently selected from $C_1$- to $C_{20}$-alkyl, where the sum of the carbon atoms of the $R^f$, $R^g$ and $R^h$ radicals is an integer from 3 to 23.

Preferred radicals of the formula (B.1) are: 1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-decyltetradecyl, 1-nonyltetradecyl, 1-octyltetradecyl, 1-heptyltetradecyl, 1-hexyltetradecyl, 1-pentyltetradecyl, 1-butyltetradecyl, 1-propyltetradecyl, 1-ethyltetradecyl, 1-methyltetradecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexyloctadecyl, 1-pentyloctadecyl, 1-butyloctadecyl, 1-propyloctadecyl, 1-ethyloctadecyl, 1-methyloctadecyl, 1-pentadecyleicosanyl, 1-tetradecyleicosanyl, 1-tridecyleicosanyl, 1-dodecyleicosanyl, 1-undecyleicosanyl, 1-butyleicosanyl, 1-propyleicosanyl, 1-ethyleicosanyl, 1-methyleicosanyl.

Particularly preferred radicals of the formula (B.1) are: 1-methylethyl, 1-methyl propyl, 1-methyl butyl, 1-methyl pentyl, 1-methyl hexyl, 1-methyl heptyl, 1-methyloctyl, 1-ethyl propyl, 1-ethyl butyl, 1-ethyl pentyl, 1-ethyl hexyl, 1-ethyl heptyl, 1-ethyloctyl, 1-propyl butyl, 1-propyl pentyl, 1-propyl hexyl, 1-propyl heptyl, 1-propyloctyl, 1-butyl pentyl, 1-butyl hexyl, 1-butyl heptyl, 1-butyloctyl, 1-pentyl hexyl, 1-pentyl heptyl, 1-pentyloctyl, 1-hexyl heptyl, 1-hexyloctyl, 1-heptyl octyl.

A particularly preferred radical of the formula (B.2) is tert.-butyl.

In a further special embodiment, $R^6$ is a radical of the formula (C.1), a radical of the formula (C.2) or a radical of the formula (C.3)

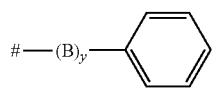

(C.1)

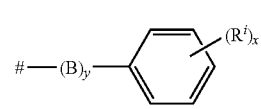

(C.2)

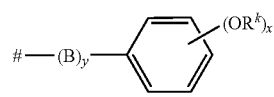

(C.3)

where

\# represents the bonding side to the nitrogen atom,

B where present, is a $C_1$-$C_{10}$-alkylene group which may be interrupted by one or more nonadjacent groups selected from —O— and —S—, y is 0 or 1, $R^i$ is independently of one another selected from $C_1$-$C_{24}$-alkyl, $C_1$-$C_{24}$-fluoroalkyl, fluorine, chlorine or bromine, $R^k$ is independently of one another selected from $C_1$-$C_{24}$-alkyl, x in formulae C.2 and C.3 is 1, 2, 3, 4 or 5.

Preferably, y is 0, i.e. the variable B is absent.

Irrespectively of its occurrence, $R^i$ is preferably selected from $C_1$-$C_{24}$-alkyl, more preferably linear $C_1$-$C_{10}$-alkyl or branched $C_3$-$C_{10}$-alkyl, especially isopropyl. Irrespectively of its occurrence, $R^k$ is preferably selected from $C_1$-$C_{30}$-alkyl, more preferably linear $C_1$-$C_{10}$-alkyl or branched $C_3$-$C_{10}$-alkyl. The variable x in formulae C.2 and C.3 is preferably 1, 2 or 3.

Examples for preferred inventive compounds of formula (I-A.2) are shown below:

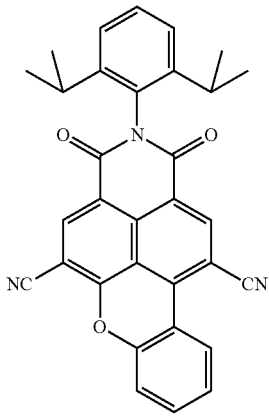

(I-A.2-1)

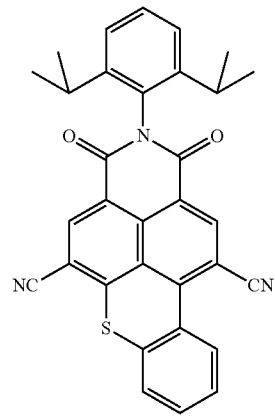

(I-A.2-2)

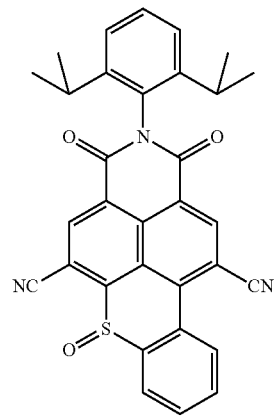

(I-A.2-3)

(I-A.2-4)
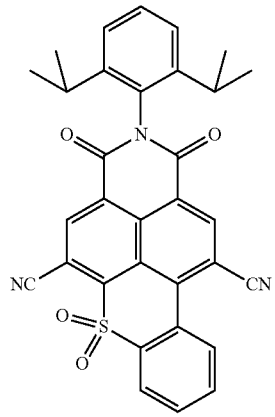
(I-A.2-5)
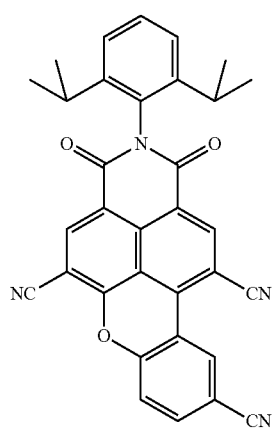
(I-A.2-6)
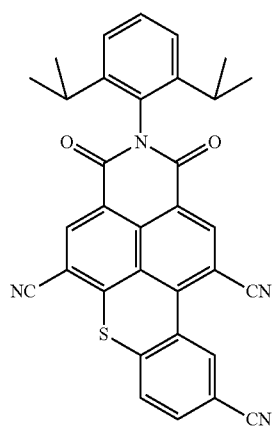
(I-A.2-7)
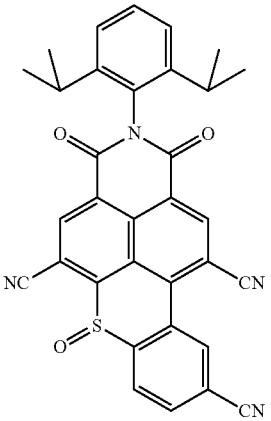
(I-A.2-8)
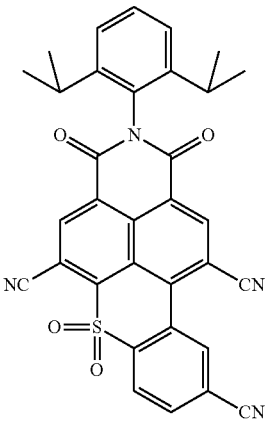
(I-A.2-9)
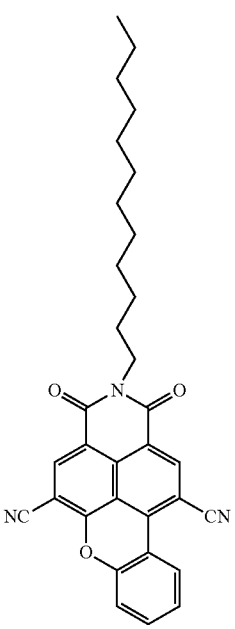

(I-A.2-10)
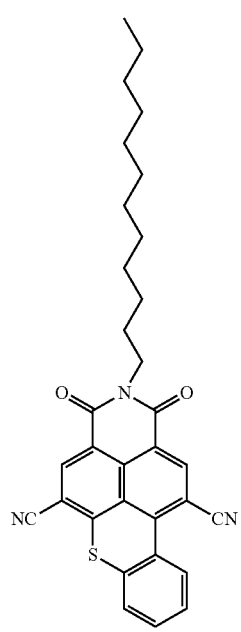
(I-A.2-11)
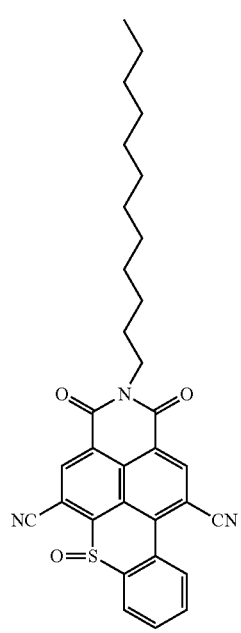
(I-A.2-12)
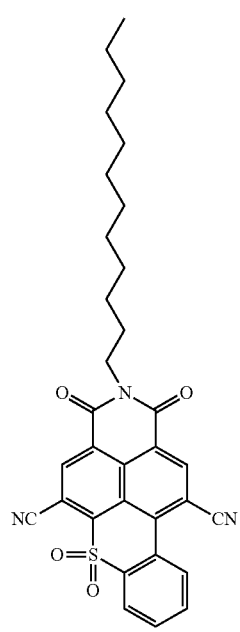
(I-A.2-13)
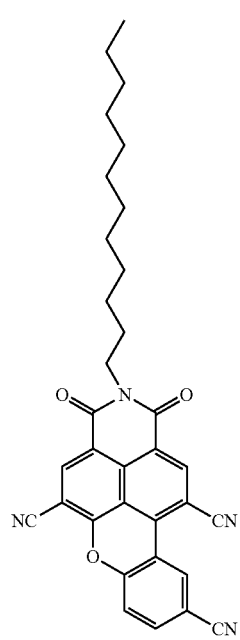

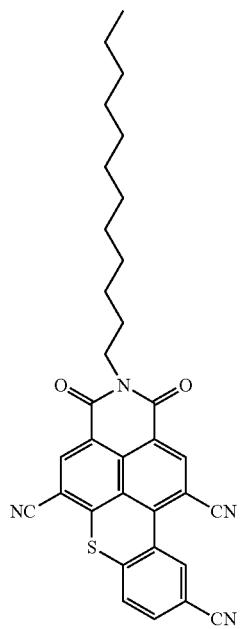
(I-A.2-14)

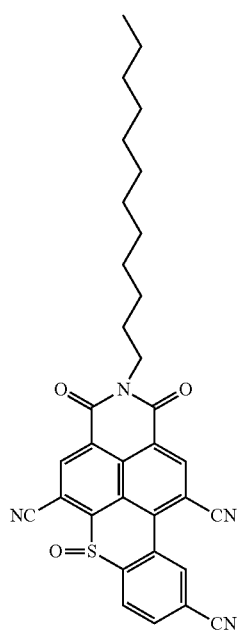
(I-A.2-15)

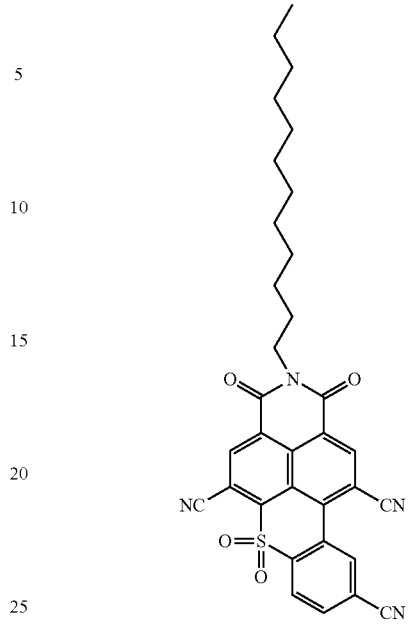
(I-A.2-16)

Amongst these compounds, more preference is given to compounds of formulae (I-A.2-1), (I-A.2.2), (I-A.2-6), (I-A.2-9), (I-A.2-10) and (I-A.2-14).

A special group of embodiments relates to compounds of formula (l-A.2), wherein the variables m, X, $R^1$, $R^2$, $R^3$, $R^4$, and $R^5$ independently of each other or in particular in combination, have the following meanings:

X is O or S;

$R^2$ and $R^4$ are each cyano;

$R^3$ and $R^5$ are each hydrogen or one of $R^3$ and $R^5$ is bromine and the other of $R^3$ and $R^5$ is hydrogen;

$R^1$ is selected from cyano, bromine, and phenyl which is unsubstituted or carries 1 or 2 radicals selected from $C_1$-$C_4$-alkyl;

$R^6$ is selected from hydrogen, $C_1$-$C_{24}$-linear alkyl, branched $C_3$-$C_{24}$-alkyl, a radical of the formula (C.1), a radical of the formula (C.2) and a radical of the formula (C.3);

m is 0 or 1.

Even more preferably,

X is O or S;

$R^2$ and $R^4$ are each cyano;

$R^3$ and $R^5$ are each hydrogen;

$R^1$ is selected from cyano, bromine, and phenyl which is unsubstituted or carries 1 or 2 radicals selected from $C_1$-$C_4$-alkyl; especially cyano;

$R^6$ is selected from linear $C_1$-$C_{24}$-alkyl, branched $C_3$-$C_{24}$-alkyl, a radical of the formula (C.1), a radical of the formula (C.2) and a radical of the formula (C.3); especially linear $C_1$-$C_{24}$-alkyl, branched $C_3$-$C_{24}$-alkyl, or phenyl which carries 1 or 2 radicals selected from $C_1$-$C_4$-alkyl such as 2,6-diisopropylphenyl;

m is 0 or 1.

According to a third group of embodiments, compounds of the formula (I) are preferred, wherein A is a radical of the formula (A.3). This group of embodiments includes the pure regioisomer of the formula (I-A.3a), the pure regioisomer of the formula (I-A.3b) and mixtures thereof,

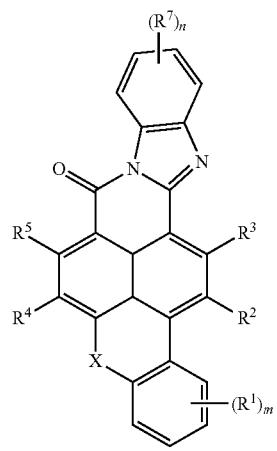

(I-A.3a)

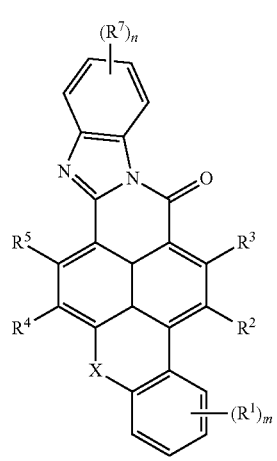

(I-A.3b)

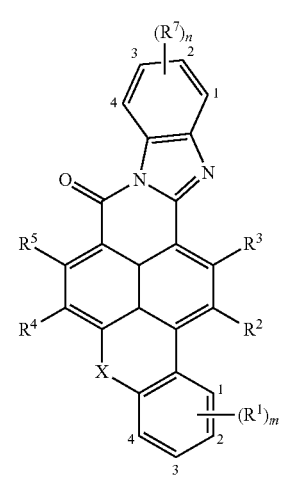

(I-A.3a)

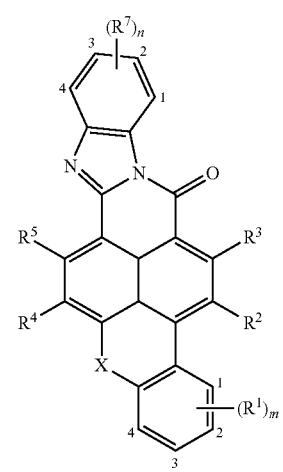

(I-A.3b)

wherein X, $R^1$, $R^2$, $R^3$, $R^4$, $R^5$, $R^7$, n and m are as defined above. In particular, X, $R^1$, $R^2$, $R^3$, $R^4$, $R^5$, and m have one of the preferred meanings mentioned above.

Preferred are compounds of the formulae (I-A.3a) and (I-A.3b), wherein n is 0, i.e. $R^7$ is absent. Preferred are also compounds of the formulae (I-A.3a) and (I-A.3b), wherein n is 1 or 2. In this context, each $R^7$ is preferably selected from cyano, bromine, chlorine, $C_1$-$C_4$-alkyl, $C_1$-$C_4$-alkoxy, $C_1$-$C_4$-haloalkyl, phenyl and phenyloxy, wherein phenyl in the two last mentioned radicals is unsubstituted or carries 1, 2 or 3 substituents selected from $C_1$-$C_{10}$-alkyl. Examples for $C_1$-$C_4$-alkyl are methyl, ethyl, n-propyl, isopropyl, n-butyl or isobutyl. Examples for $C_1$-$C_4$-alkoxy are methoxy, ethoxy, n-propoxy, isopropoxy, n-butoxy or isobutoxy. $C_1$-$C_4$-haloalkyl is in particular $C_1$-$C_2$-haloalkyl. In particular, $R^7$ is selected from cyano, bromine and phenyl which is unsubstituted or carries 1 or 2 radicals selected from $C_1$-$C_4$-alkyl.

Examples for such preferred compounds are given in tables 1 to 4. Table 1: Compounds of the formulae (I-A.3a) or (I-A.3b) and their mixtures, wherein X is O, and wherein $R^2$, $R^3$, $R^4$, $R^5$, $(R^1)_m$ and $(R^7)_n$ have the meanings given in any of lines 1 to 10 of table A.

TABLE A

| | $R^2$ | $R^4$ | $R^3$ | $R^5$ | $(R^1)_m$ | $(R^7)_n$ |
|---|---|---|---|---|---|---|
| 1. | CN | CN | H | H | — | — |
| 2. | CN | CN | H | H | — | 1-Ph, 4-Ph |
| 3. | CN | CN | H | H | — | 1-Ph, 3-Ph |
| 4. | CN | CN | H | H | — | 2-Ph, 3-Ph |
| 5. | CN | CN | H | H | — | 2-Ph, 4-Ph |
| 6. | CN | CN | H | H | 2-CN | — |
| 7. | CN | CN | H | H | 2-CN | 1-Ph, 4-Ph |
| 8. | CN | CN | H | H | 2-CN | 1-Ph, 3-Ph |
| 9. | CN | CN | H | H | 2-CN | 2-Ph, 3-Ph |
| 10. | CN | CN | H | H | 2-CN | 2-Ph, 4-Ph |

In table A the sign "--" in the definition of $(R^1)_m$ has the meaning of m being 0, i.e. $R^1$ is absent; the sign "--" in the definition of $(R^7)_n$ has the meaning of n being 0, i.e. $R^7$ is absent; in case that m is different from 0, the number in the definition of $(R^1)_m$ indicates the position the radical $R^1$ is attached to the aromatic ring; in case that n is different from 0, the numbers in the definition of $(R^7)_n$ indicate the positions the radicals $R^7$ are attached to the benzimidazole ring; Ph is phenyl.

Amongst the compounds of the formulae (I-A.3a) or (I-A.3b), preference is also given to the compounds defined in the following tables 2, 3 and 4:

Table 2:

Compounds of the formulae (I-A.3a) or (I-A.3b) and their mixtures, wherein X is S, and wherein $R^2$, $R^3$, $R^4$, $R^5$, $(R^1)_m$ and $(R^7)_n$ have the meanings given in any of lines 1 to 10 of table A.

Table 3:

Compounds of the formulae (I-A.3a) or (I-A.3b) and their mixtures, wherein X is SO, and wherein $R^2$, $R^3$, $R^4$, $R^5$, $(R^1)_m$ and $(R^7)_n$ have the meanings given in any of lines 1 to 10 of table A.

Table 4:

Compounds of the formulae (I-A.3a) or (I-A.3b) and their mixtures, wherein X is $SO_2$, and wherein $R^2$, $R^3$, $R^4$, $R^5$, $(R^1)_m$ and $(R^7)_n$ have the meanings given in any of lines 1 to 10 of table A.

Amongst the compounds of the formulae (I-A.3a) or (I-A.3b) and their mixtures, special preference is given to those compounds, where X is O; and $R^2$, $R^3$, $R^4$, $R^5$, $(R^1)_m$ and $(R^7)_n$ have the meanings given in line 1 of table A.

Amongst the compounds of the formulae (I-A.3a) or (I-A.3b) and their mixtures, special preference is also given to those compounds, where X is S; and $R^2$, $R^3$, $R^4$, $R^5$, $(R^1)_m$ and $(R^7)_n$ have the meanings given in line 1 of table A.

According to a fourth group of embodiments, compounds of the formula (I) are preferred, wherein A is a radical of the formula (A.4). This group of embodiments includes the pure regioisomer of the formula (I-A.4a), the pure regioisomer of the formula (I-A.4b) and mixtures thereof,

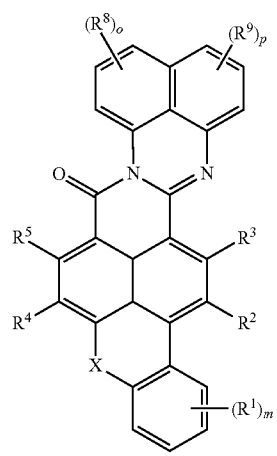

(I-A.4a)

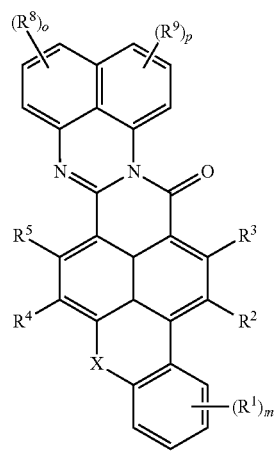

(I-A.4b)

wherein X, $R^1$, $R^2$, $R^3$, $R^4$, $R^5$, $R^8$, $R^9$, o, p and m are as defined above. In particular, X, $R^1$, $R^2$, $R^3$, $R^4$, $R^5$, and m have one of the preferred meanings mentioned above.

Preferred are compounds of the formulae (I-A.4a) or (I-A.4b) and their mixtures, wherein o and p are 0, i.e. $R^8$ and $R^9$ are absent. Preferred are also compounds of the formulae (I-A.4a) and (I-A.4b), wherein the sum of o and p is 1, 2, 3 or 4. In this context, $R^8$ and $R^9$ are, independently of each other, preferably selected from cyano, bromine, chlorine, $C_1$-$C_4$-alkyl, $C_1$-$C_4$-alkoxy, $C_1$-$C_4$-haloalkyl, phenyl and phenyloxy, wherein phenyl in the two last mentioned radicals is unsubstituted or carries 1, 2 or 3 substituents selected from $C_1$-$C_{10}$-alkyl. Examples for $C_1$-$C_4$-alkyl are methyl, ethyl, n-propyl, isopropyl, n-butyl or isobutyl. Examples for $C_1$-$C_4$-alkoxy are methoxy, ethoxy, n-propoxy, isopropoxy, n-butoxy or isobutoxy. $C_1$-$C_4$-haloalkyl, in particular $C_1$-$C_2$-haloalkyl. In particular, $R^8$ and $R^9$ are, independently of each other, selected from cyano, bromine and phenyl which is unsubstituted or carries 1 or 2 radicals selected from $C_1$-$C_4$-alkyl.

Examples for preferred inventive compounds of formulae (l-A.4a) and (l-A.4b) are shown below:

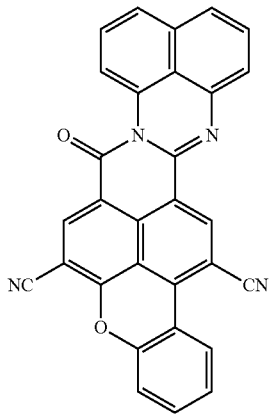

(I-A.4a-1)

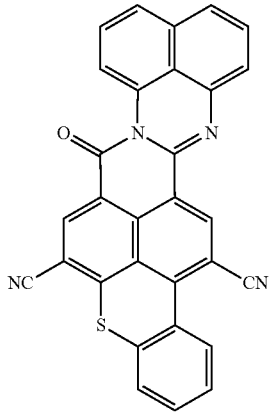

(I-A.4a-2)

(I-A.4a-3)
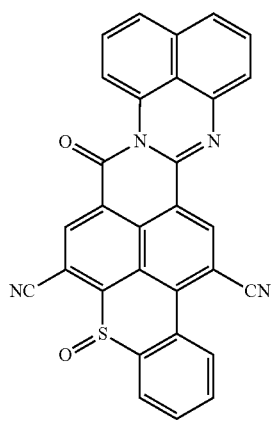
(I-A.4a-6)
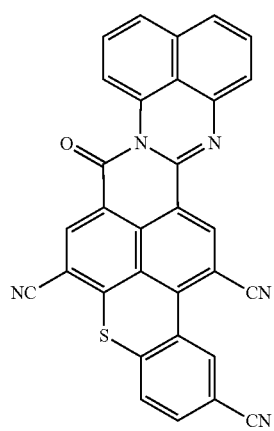
(I-A.4a-4)
(I-A.4a-7)
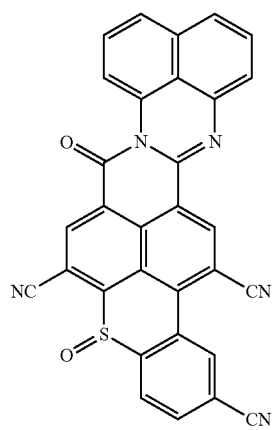
(I-A.4a-5)
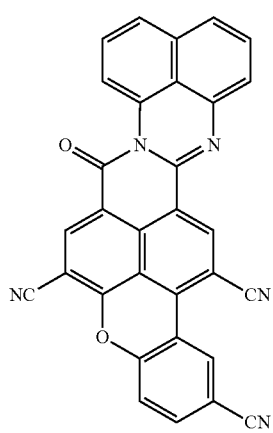
(I-A.4a-8)
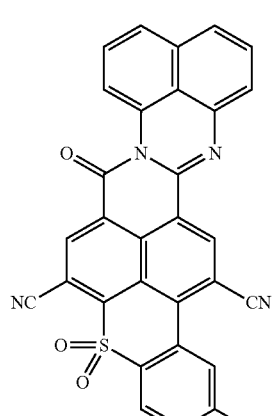

(I-A.4b-1)
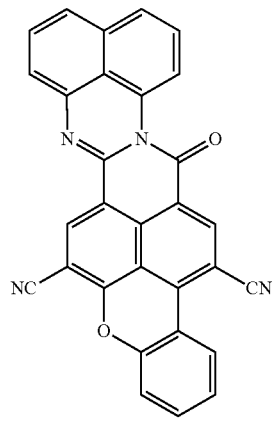
(I-A.4b-4)
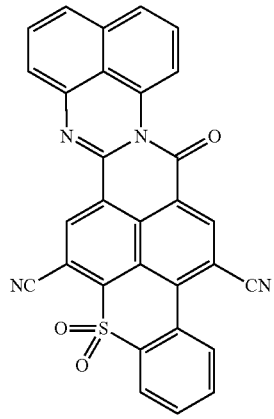
(I-A.4b-2)
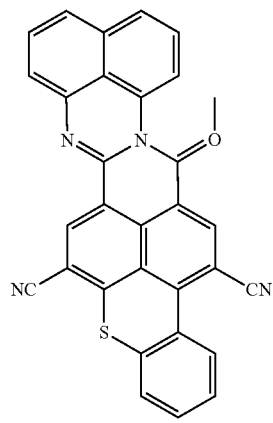
(I-A.4b-5)
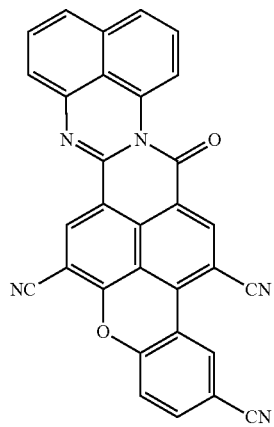
(I-A.4b-3)
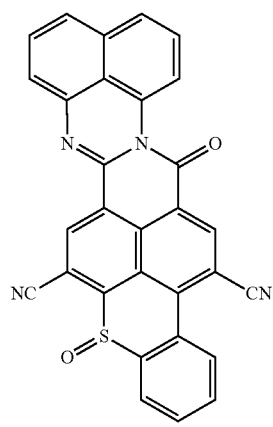
(I-A.4b-6)
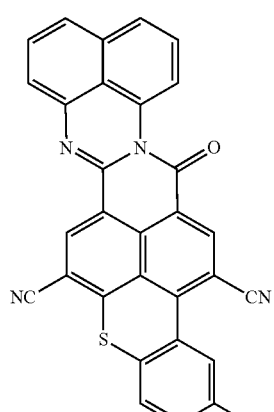

-continued

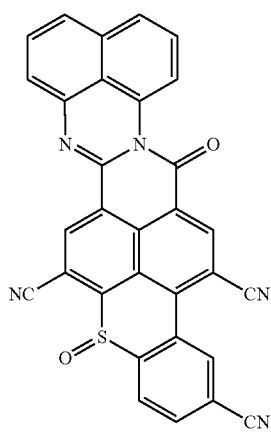

(I-A.4b-7)

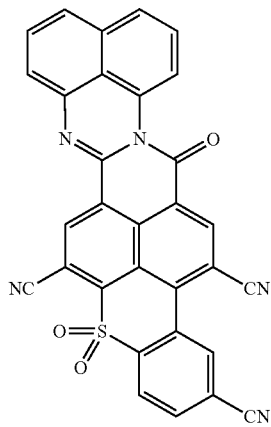

(I-A.4b-8)

In particular, in the compounds of formula (I), A is a radical of formulae (A.2), (A.3) or (A.4). In a specific embodiment of the present invention, in the compounds of the formula (I), A is a radical of formulae (A.2), (A.3) or (A.4) and X is O or S.

Compounds of the formula (I) according to the present invention can be prepared e.g. according to the preparation methods as described below or in the experimental part of this application.

Thus, a particular suitable method for preparing compounds of formula (I)

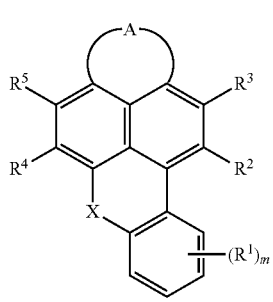

(I)

wherein X, A, $R^1$, $R^2$, $R^3$, $R^4$, $R^5$ and m are as defined above, comprises the following steps:
a) providing a compound of formula (III)

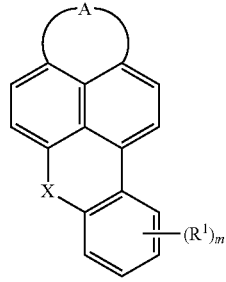

(III)

b) reacting the compound of formula (III) with a halogenating agent of formula selected from a brominating agent or a chlorinating agent to give a compound of compound of formula (II)

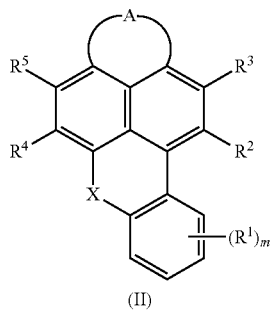

(II)

wherein
at least one of the radicals $R^2$, $R^3$, $R^4$ and $R^5$ is halogen selected from chlorine or bromine and the remaining radicals are each hydrogen, with the proviso that radicals different from hydrogen have the same meaning; and
c) subjecting the compound of the formula (II) obtained in step b) to a substitution of halogen by cyano to give a compound of formula (I).

Step a)

Benzoxanthene compounds or benzothioxanthene compounds of formula (III), where A is a radical of formulae (A.1), (A.2) or (A.3) are known in the art and for example described in U.S. Pat. No. 3,748,330, U.S. Pat. No. 3,812,051, GB 1 440 450, WO 2014/131628 or WO 2015/062916. Compounds of formula (III), where A is a radical of formula (A.4) can be prepared in analogy to the methods for preparing a compound of formula (III), where A is a radical (A.3). Especially, benzoxanthene compounds of formula (III) can advantageously prepared as described below.

Step b)

Bromination is typically carried out with elemental bromine in a solvent as described e.g. in WO 2014/131628.

Further suitable brominating agents are N-bromosuccinimide and dibromoisocyanuric acid. Suitable solvents are water or aliphatic monocarboxylic acids, and chlorinated hydrocarbons such as chlorobenzene and chloroform. Suitable aliphatic monocarboxylic acids are those having 2 to 6 carbon atoms, such as acetic acid, propionic acid, butyric acid, pentanecarboxylic acid and hexanecarboxylic acid, and mixtures thereof. When an aliphatic monocarboxylic acid is used as a solvent, it may be advantageous to use iodine as a catalyst.

Chlorination is typically carried out with elemental chlorine, N-chlorosuccinimide, chlorosulfonic acid, sulfuryl chloride in an inert solvent as described e.g. in US 2011/0068328. A further suitable chlorinating agent is N-chlorosuccinimide.

Depending on the molar ratio of the halogenating agent to compound of the formula (III), a mono-, di- or multihalogene-substituted compound of formula (II), i.e. a mono-, di-, or multibromo-substituted compound of formula (II) and mono-, di- or multichlorine-substituted compound of formula (II), respectively, is obtained which can be separated by column chromatography ($SiO_2$).

Step c)

A suitable cyanating agent is for example copper(I) cyanide. Suitable process conditions for the exchange of bromine or chlorine with cyano are described e.g. in J. March, Advanced Organic Chemistry, 4th edition, John Wiley & Sons Publishers (1992), p. 660-661, in WO 2004/029028 and WO 2015/019270.

Compounds of the formula (II), wherein X is S, SO or $SO_2$ are also novel and are especially useful as intermediate compounds in the preparation of compounds I. Thus, a further aspect of the present invention relates to novel compounds of formula (II), wherein X is S, SO or $SO_2$.

Compounds of formula (III), where X is O, i.e. benzo[k,l]xanthene compounds of formula (III.1),

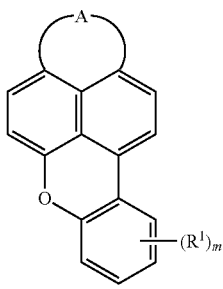

(III.1)

where $(R^1)_m$, is as defined above, and
A is a radical of formulae (A.1), (A.2), (A.3) or (A.4);
are useful intermediates in the preparation of compounds of formula (I), where X is O.

WO 2014/131628 discloses a three-step process for preparing 2-(2,6-diisopropylphenyl)-1H-xantheno[2,1,9-def]isoquinoline-1,3(2H)-dione, i.e. compounds of formula (III.1), where A is a 2,6-diisopropylphenyl and m is 0, i.e. $R^1$ is absent. The total yield over the three steps is 10.9%.

According to WO 2014/131628, the compound is prepared by
(1) reacting 6-chloro-2-(2,6-diisopropylphenyl)-1H-benzo[de]isoquinoline-1,3(2H)-dione with 2-nitrophenol in the presence of potassium carbonate to give 4-(2-nitrophenoxy)-N-(2,6-diisopropylphenyl)-1,8-naphthalimide in 71% yield.

(2) reducing 4-(2-nitrophenoxy)-N-(2,6-diisopropylphenyl)-1,8-naphthalimide to 4-(2-aminophenoxy)-N-(2,6-diisopropylphenyl)-1,8-naphthalimide by catalytic hydrogenation using Pd/C in 90% yield.
(3) diazotiation of 4-(2-aminophenoxy)-N-(2,6-diisopropylphenyl)-1,8-naphthalimide followed by treatment with copper(II) sulfate to give 2-(2,6-diisopropylphenyl)-1H-xantheno[2,1,9-def]isoquinoline-1,3(2H)-dione in 17% yield.

WO 2015/062916 discloses a four-step process for preparing a mixture of 8H-benzo[3,4]isochromeno[7,8,1-def]benzo[4,5]imidazo[1,2-b]isoquinolin-8-one 2410A and 7H-benzo[3,4] isochromeno[7,8,1-def]benzo[4,5]imidazo[2,1-a]isoquinolin-7-one 2410B

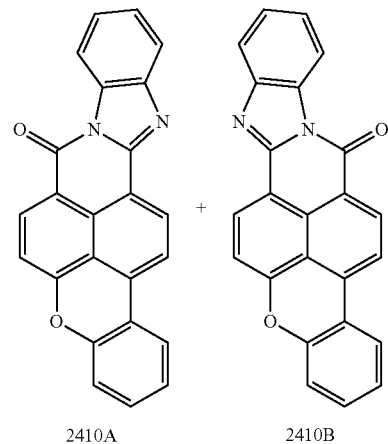 [SMILES: O=c1c2ccc3oc4ccccc4c4ccc(c2c34)c2nc3ccccc3n12 ; O=c1c2ccc3c4ccccc4oc4ccc(c2c43)c2nc3ccccc3n12]

2410A    2410B i.e. compounds of formula (III.1), where A is a radical of formula (A.3), n is 0 and m is 0, i.e. $R^7$ and $R^1$ are absent. The total yield over the four steps is 1.7%.

According to WO 2015/062916, the mixture of compounds 2410A and 2410B is prepared by
(1) reacting 4-bromonaphthalic anhydride with 2-nitrophenol in the presence of copper powder and sodium hydroxide to give 4-(2-nitrophenoxy)-1,8-naphthalic anhydride in a yield of 10%;
(2) reducing 4-(2-nitrophenoxy)-1,8-naphthalic anhydride to 4-(2-aminophenoxy)-1,8-naphthalic anhydride by catalytic hydrogenation using Pd/C in a yield of 95%;
(3) diazotiation of 4-(2-aminophenoxy)-1,8-naphthalic anhydride followed by treatment with copper(II) sulfate to give benzo[k,l]xanthene-3,4-dicarboxylic anhydride in 21% yield;
(4) reacting benzo[k,l]xanthene-3,4-dicarboxylic anhydride with o-phenylendiamine to give a mixture of 8H-benzo[3,4]isochromeno[7,8,1-def]benzo[4,5]imidazo[1,2-b]isoquinolin-8-one 2410A and 7H-benzo[3,4] isochromeno[7,8,1-def]benzo[4,5]imidazo[2,1-a]isoquinolin-7-one 2410B in 83% yield.

According to each of the synthetic routes of WO 2014/131628 and WO 2015/062916, the benzo[k,l]xanthene-skeleton is prepared by a Pschorr cyclization in a moderate yield. Thus, these routes are not very attractive for preparing the compounds of formula (I), where X is O. When starting from readily available starting materials, the total number of reaction steps required for the preparation of compounds of formula (III.1) according to prior art is high and overall yields are low.

Therefore, it is an object of the present invention to provide a process for the preparation of compounds of formula (III.1) which overcomes the problems associated with the processes of prior art.

It has now surprisingly been found that compounds of the formula (III.1) can be prepared by reacting a 4,5-dihalogen-naphthalenedicarboxylic acid derivate of formula (VII) with a boronic acid derivative of formula (VIII) in the presence of a base and a transition metal catalyst in the sense of a tandem Suzuki phenoxylation reaction as depicted in Scheme 1.

Scheme 1:

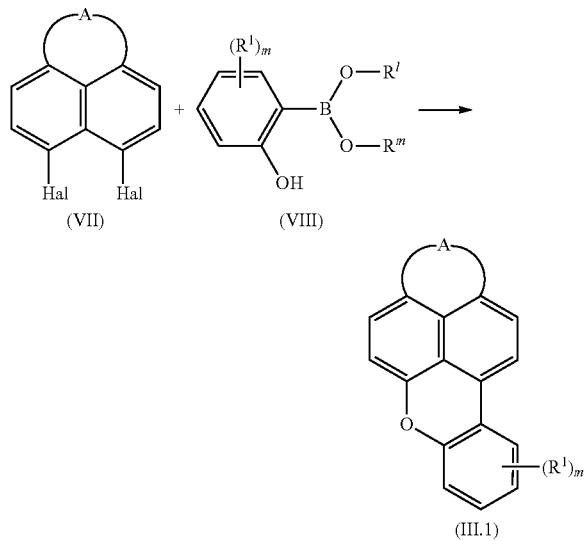

In Scheme 1, Hal in each case is chlorine or bromine; $R^l$ and $R^m$ are each independently hydrogen or $C_1$-$C_4$-alkyl, or $R^l$ and $R^m$ together form an 1,2-ethylene or 1,2-propylene moiety the carbon atoms of which may be unsubstituted or may all or in part be substituted by methyl groups.

The reaction is carried out in the presence of a base and a transition metal catalyst, in particular a palladium catalyst, such as for example described in the following literature: Synth. Commun. Vol. 11, p. 513 (1981); Acc. Chem. Res. Vol. 15, pp. 178-184 (1982); Chem. Rev. Vol. 95, pp. 2457-2483 (1995); Organic Letters Vol. 6 (16), p. 2808 (2004); "Metal catalyzed cross coupling reactions", $2^{nd}$ Edition, Wiley, VCH 2005 (Eds. De Meijere, Diederich); "Handbook of organopalladium chemistry for organic synthesis" (Eds Negishi), Wiley, Interscience, New York, 2002; "Handbook of functionalized organometallics", (Ed. P. Knochel), Wiley, VCH, 2005.

Suitable catalysts are in tetrakis(triphenylphosphine)palladium(0); bis(triphenylphosphine)palladium(II) chloride; bis(acetonitrile)palladium(II) chloride; [1,1'-bis(diphenylphosphino)ferrocene]-palladium(II) chloride/methylene chloride (1:1) complex; bis[bis-(1,2-diphenylphosphino)ethane]palladium(0); bis(bis-(1,2-diphenylphosphino)butane]-palladium(II) chloride; palladium(II) acetate; palladium(II) chloride; and palladium(II) acetate/tri-o-tolylphosphine complex or mixtures of phosphines and Pd salts or phosphines and Pd-complexes e.g. dibenzylideneacetone-palladium and tri-tert-butylphosphine (or its tetrafluoroborate), tricyclohexylphosphine; or a polymer-bound Pd-triphenylphosphine catalyst system, such as polystyrene-bound Pd-triphenylphosphine catalyst system.

Suitable bases are, in general, inorganic compounds, such as alkali metal and alkaline earth metal oxides, such as lithium oxide, sodium oxide, calcium oxide and magnesium oxide, alkali metal and alkaline earth metal carbonates, such as lithium carbonate, sodium carbonate, potassium carbonate, caesium carbonate and calcium carbonate, and also alkali metal bicarbonates, such as sodium bicarbonate, alkali metal and alkaline earth metal alkoxides, such as sodium methoxide, sodium ethoxide, potassium ethoxide and potassium tert.-butoxide, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to bases such as sodium carbonate, potassium carbonate, caesium carbonate, triethylamine and sodium bicarbonate.

The base is used in a 1:1 to 1:10, preferably a 1:1.5 to 5 molar ratio relative to 1 mole of compound (VII), the boronic acid derivative of formula (VIII) is used in a 1:1 to 1:5 ratio, preferably a 1:1.5 to 1:3.5 molar ratio relative to 1 mole of compounds (VII).

The reaction is usually carried out in an inert organic solvent. Suitable solvents are aliphatic hydrocarbons, such as pentane, hexane, cyclohexane and petroleum ether, aromatic hydrocarbons, such as toluene, o-, m- and p-xylene, ethers, such as diisopropyl ether, tert.-butyl methyl ether, dioxane, anisole and tetrahydrofuran and dimethoxyethane, ketones, such as acetone, methyl ethyl ketone, diethyl ketone and tert.-butyl methyl ketone, and also dimethyl sulfoxide, dimethylformamide and dimethylacetamide, particularly preferably ethers, such as tetrahydrofuran, dioxane and dimethoxyethane. It is also possible to use mixtures of the solvents mentioned, or mixtures with water.

The reaction is usually carried out at temperatures of from 20° C. to 180° C., preferably from 40° C. to 120° C.

The required starting compounds of the formulae (VII) and (VIII)I are known or can be prepared by synthesis processes known for these classes of compounds.

In comparison to the already known processes, the novel process for preparing compounds of the formula (III.1) allows a convergent synthesis of the compound of formula (I.1) in high yields from readily accessible starting materials, thereby allowing to avoid the problems associated with the processes of prior art.

Compounds of the formula (I), wherein X is SO or $SO_2$, can be obtained by oxidizing compounds of the formula (I), wherein X is S. Suitable oxidizing agents are meta-chloroperbenzoic acid, hypochlorite or hydrogen peroxide.

Other inventive compounds not described above may be prepared in analogy to the methods described therein.

The present invention further provides color converters comprising at least one polymer as a matrix material and at least one cyanated compound of the formula I or mixtures thereof as defined above as a fluorescent dye. In particular, the at least one compound of formula (I) is selected from compounds of formulae I-A.1-1 to I-A.1-8. Likewise, in particular, the at least one compound of formula (I) is selected from compounds and I-A.2-1 to I-A.2-16. Likewise in particular, the at least one compound of formula (I) is selected from compounds of formula I-A.3a, I-A.3b and their mixtures as defined in tables 1, 2, 3 and 4 above. Likewise in particular, the at least one compound of formula (I) is selected from compounds of formula I-A.4a-1 to I-A.4a-8, I-A.4b-1 to I-A.4b-8.

Suitable polymers are in principle all polymers capable of dissolving or homogeneously dispersing the at least one cyanated compound of the formula I or mixtures in a sufficient amount.

Suitable polymers may be inorganic polymers or organic polymers.

In a preferred embodiment, the organic polymers consist essentially of polystyrene, polycarbonate, polymethylmethacrylate, polyvinylpyrrolidone, polymethacrylate, polyvinyl acetate, polyvinyl chloride, polybutene, silicone, polyacrylate, epoxy resin, polyvinyl alcohol, poly(ethylene vinylalcohol)-copolymer (EVA, EVOH), polyacrylonitrile, polyvinylidene chloride (PVDC), polystyreneacrylonitrile (SAN), polybutylene terephthalate (PBT), polyethylene terephthalate (PET), polyvinyl butyrate (PVB), polyvinyl chloride (PVC), polyamides, polyoxymethylenes, polyimides, polyetherimides or mixtures thereof.

Preferably, the at least one polymer consists essentially of polystyrene (PS), polycarbonate (PC), polymethylmethacrylate (PMMA), polyethylene terephthalate (PET) or mixtures thereof.

Most preferably, the at least one polymer consists essentially of polyethylene terephthalate, polystyrene or polycarbonate.

Polyethylene terephthalate is obtainable by condensation of ethylene glycol with terephthalic acid.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as paramethoxystyrene, para-butoxystyrene, para-tert-butoxystyrene.

In general, suitable polystyrenes have a mean molar mass $M_n$ of 10 000 to 1 000 000 g/mol (determined by GPC), preferably 20 000 to 750 000 g/mol, more preferably 30 000 to 500 000 g/mol.

In a preferred embodiment, the matrix of the color converter consists essentially or completely of a homopolymer of styrene or styrene derivatives.

In further preferred embodiments of the invention, the matrix consists essentially or completely of a styrene copolymer, which are likewise regarded as polystyrene in the context of this application. Styrene copolymers may comprise, as further constituents, for example, butadiene, acrylonitrile, maleic anhydride, vinylcarbazole or esters of acrylic, methacrylic or itaconic acid as monomers. Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylonitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS).

A further preferred polymer is alpha-methylstyrene-acrylonitrile copolymer (AMSAN).

The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization.

The preparation of suitable polystyrenes is described, for example, in Oscar Nuyken, Polystyrenes and Other Aromatic Polyvinyl Compounds, in Kricheldorf, Nuyken, Swift, New York 2005, p. 73-150 and references cited therein; and in Elias, Macromolecules, Weinheim 2007, p. 269-275.

Polycarbonates are polyesters of carbonic acid with aromatic or aliphatic dihydroxyl compounds. Preferred dihydroxyl compounds are, for example, methylenediphenylenedihydroxyl compounds, for example bisphenol A.

One means of preparing polycarbonates is the reaction of suitable dihydroxyl compounds with phosgene in an interfacial polymerization. Another means is the reaction with diesters of carbonic acid such as diphenyl carbonate in a condensation polymerization.

The preparation of suitable polycarbonates is described, for example, in Elias, Macromolecules, Weinheim 2007, p. 343-347.

In a preferred embodiment, polymers which have been polymerized with exclusion of oxygen are used. Preferably, the monomers during the polymerization comprised a total of not more than 1000 ppm of oxygen, more preferably not more than 100 ppm and especially preferably not more than 10 ppm.

Suitable polymers may comprise, as further constituents, additives such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers such as phosphites or phosphonites, as sold, for example, by BASF under the Irgafos® trade name.

Suitable UV absorbers are, for example, benzotriazoles such as 2-(2-hydroxyphenyl)-2H-benzotriazole (BTZ), triazines such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment, $TiO_2$ is used as the sole UV absorber.

In a preferred embodiment of the invention, suitable polymers do not comprise any antioxidants or free-radical scavengers.

In a further embodiment of the invention, suitable polymers are transparent polymers.

In another embodiment, suitable polymers are opaque polymers.

The polymers mentioned serve as matrix material for suitable organic fluorescent dyes.

The inventive fluorescent dyes, i.e. the cyanated compounds of the formula I and mixtures thereof, may either be dissolved in the polymer or may be in the form of a homogeneously distributed mixture. The fluorescent dyes are preferably dissolved in the polymer.

In a preferred embodiment, color converters comprise, as well as the at least one inventive fluorescent dye of the compound of the formula I or mixtures thereof, further fluorescent colorants. For example, the at least one inventive organic fluorescent dye can be combined with a red-fluorescing fluorescent colorant. In many cases, fluorescent colorants are combined with one another such that color converters which can convert blue light to white light with good color rendering index are obtained.

Suitable further fluorescent colorants are, for example, inorganic fluorescent colorants. Particularly preferred among these are those from the class of the rare earth-doped aluminates, silicates, nitrides and garnets. Further inorganic lighting colorants are, for example, those mentioned in "Luminescence—from Theory to Applications", Cees Ronda [ed.], Wiley-VCH, 2008, Chapter 7, "Luminescent Materials for Phosphor-Converted LEDs", Th. Jüstel, pages 179-190.

Garnets are compounds of the general formula $X_3Y_2[ZO_4]_3$ in which Z is a divalent cation such as Ca, Mg, Fe, Mn, Y is a trivalent cation such as Al, Fe, Cr, rare earths, and Z is Si, Al, $Fe^{3+}$, $Ga^{3+}$. The garnet is preferably yttrium aluminum garnet $Y_3Al_5O_{12}$ doped with $Ce^{3+}$, $Gd^{3+}$, $Sm^{3+}$, $Eu^{2+}$, $Eu^{3+}$, $Dy^{3+}$, $Tb^{3+}$ or mixtures thereof.

Suitable nitrides are described, for example, in U.S. Pat. No. 8,274,215. Suitable silicates are described, for example, in U.S. Pat. No. 7,906,041 and U.S. Pat. No. 7,311,858.

Suitable aluminates are described, for example, in U.S. Pat. No. 7,755,276.

Suitable aluminate phosphors of the formula $SrLu_{2-x}Al_4O_{12}:Ce_x$ in which x is a value from the range from 0.01 to 0.15 are known from WO2012010244. Luminophores of the composition $MLn_2QR_4O_{12}$ where M is at least one of the elements Mg, Ca, Sr or Ba, Ln is at least one of the elements Sc, Y, La, Ce, Pr, Nd, Sm, Eu, Gd, Tb, Dy, Ho, Er, Tm, Yb and Lu; Q is one of the elements Si, Ge, Sn, and Pb, and R, finally, is at least one of the elements B, Al, Ga, In and Tl are known from US 2004/0062699.

In addition, all organic red or pink fluorescent dyes are particularly suitable. In another embodiment, further fluorescent colorants comprise further orange- or yellow-fluorescing fluorescent dyes. Suitable organic fluorescent red dyes have, for example, the general formula

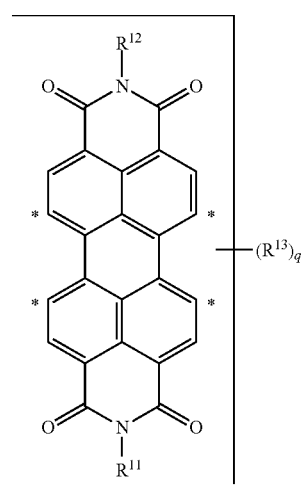

(IV)

where
q is 1, 2, 3, or 4;
$R^{11}$, $R^{12}$ are each independently $C_1$-$C_{30}$-alkyl, $C_3$-$C_8$-cycloalkyl, aryl, hetaryl, aryl-$C_1$-$C_{10}$-alkylene, where the aromatic ring in the three latter radicals is unsubstituted or mono- or polysubstituted by $C_1$-$C_{10}$-alkyl, and
$R^{13}$ is $C_6$-$C_{10}$-aryloxy which is unsubstituted or mono- or polysubstituted by halogen, $C_1$-$C_{10}$-alkyl or $C_6$-$C_{10}$-aryl, where the $R^{13}$ radicals are at one or more of the positions indicated by*.

A particular embodiment relates to color converters, wherein the at least one further organic fluorescent dye of formula (IV) is different from N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide or mixtures thereof.

Preferably, $R^{11}$ and $R^{12}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{11}$ and $R^{12}$ are identical. Very particularly, $R^{11}$ and $R^{12}$ are each 2,6-diisopropylphenyl or 2,4-di-tert-butylphenyl.

$R^{13}$ is preferably phenoxy, phenylphenoxy or ($C_1$-$C_{10}$-alkyl)phenoxy, more preferably 2,6-(diphenyl)phenoxy, 2,6-(dialkyl)phenoxy or 2,4-(dialkyl)phenoxy. Especially preferably $R^{13}$ is phenoxy, 2,6-diphenylphenoxy, 2,6-diisopropylphenoxy, 2,4-di-tert-butylphenoxy or 4-tert-octylphenoxy.

More particularly, suitable further organic fluorescent dyes are selected from the compounds of the formulae IV-1, IV-2 and IV-3

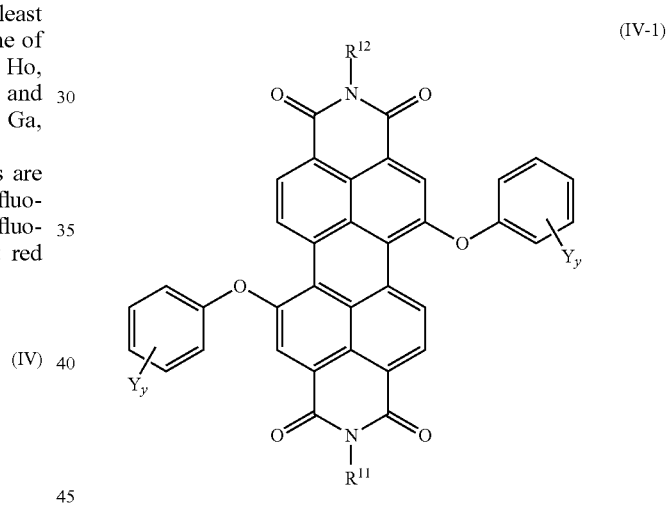

(IV-1)

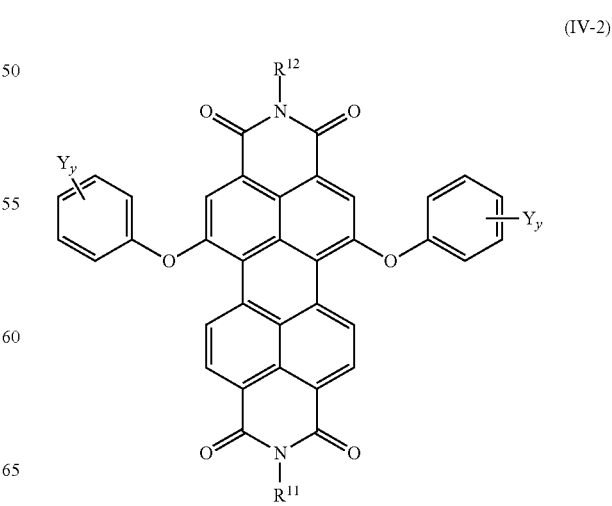

(IV-2)

-continued

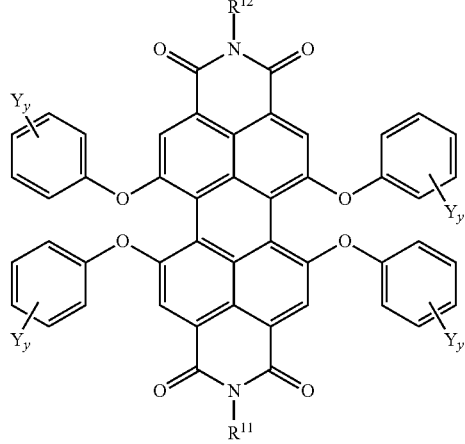
(IV-3)

in which
R$^{11}$ and R$^{12}$ are each as defined above and especially have one of the preferred meanings;
Y is linear or branched C$_1$-C$_{10}$-alkyl or phenyl; and
y is 0, 1, 2, or 3.

Further examples of particularly suitable further organic fluorescent dyes are the perylene derivatives specified in WO2007/006717 at page 1 line 5 to page 22 line 6.

Particularly suitable further organic fluorescent dyes are
N,N'-bis2,6-diisopropylphenyl)-1,6,7,12-tetraphenoxyperylene-3,4;9,10-tetracarboximide, N,N'-bis(2,6-diisopropylphenyl)-1,7-di(p-tert-octylphenoxy)perylene-3,4;9,10-tetracarboximide, N,N'-bis(2,6-diisopropylphenyl)-1,6-di(p-tert-octylphenoxy)perylene-3,4;9,10-tetracarboximide, N,N'-bis(2,6-diisopropylphenyl)-1,7-diphenoxyperylene-3,4;9,10-tetracarboximide, N,N'-bis(2,6-diisopropylphenyl)-1,6-diphenoxyperylene-3,4;9,10-tetracarboximide, N,N'-bis(2,6-diisopropylphenyl)-1,7-di(2,6-diphenyllphenoxy)perylene-3,4;9,10-tetracarboximide, N,N'-bis(2,6-diisopropylphenyl)-1,6-di(2,6-diphenylphenoxy)perylene-3,4;9,10-tetracarboximide and mixtures thereof.

Likewise preferably, the further organic fluorescent dye is selected from N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide and mixtures thereof.

In a further embodiment, inventive color converters additionally comprise at least one further organic fluorescent dye of the formulae

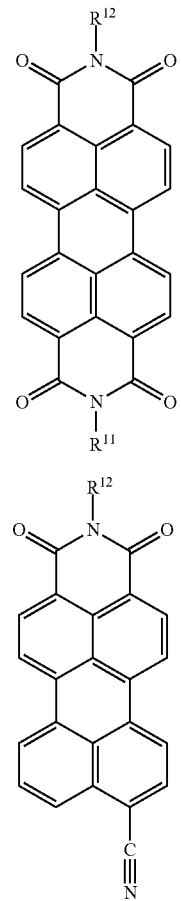
(V)

(VI)

where R$^{11}$ and R$^{12}$ are each as defined above.

In one embodiment of the invention, inventive color converters have a laminate structure. They may either have a monolayer structure or a multilayer structure, generally composed of a plurality of polymer layers comprising one or more fluorescent colorants and/or scattering bodies.

In one embodiment, the color converters consist of a plurality of polymer layers which have been laminated together to form a composite and wherein the various fluorescent colorants and/or scattering bodies may be present in different polymer layers.

If inventive color converters comprise more than one fluorescent colorant, it is possible in one embodiment of the invention for a plurality of fluorescent colorants to be present alongside one another in one layer.

In another embodiment, the various fluorescent colorants are present in various layers.

In a preferred embodiment, inventive color converters comprise, as well as the at least one organic fluorescent dye present in accordance with the invention, at least one further organic fluorescent dye of formula (IV), scattering bodies based on TiO$_2$ and at least one polymer consisting essentially of polystyrene, polyethylene terephthalate (PET) or polycarbonate.

In a further preferred embodiment, inventive color converters comprise, as well as the at least one organic fluorescent dye present in accordance with the invention, at least one further organic fluorescent dye of formula (IV) and at least one further organic fluorescent dye of formula (V) or (VI), scattering bodies based on TiO$_2$ and at least one polymer consisting essentially of polystyrene, polyethylene terephthalate (PET) or polycarbonate.

In a particularly preferred embodiment, inventive color converters comprise, as well as the at least one organic fluorescent dye present in accordance with the invention, at least one further red organic fluorescent dye selected from N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide, and at least one further organic fluorescent dye selected from N,N'-bis(2,6-diisopropylphenyl)perylene-3,4;9,10-tetracarboximide or N'-(2,6-diisopropylphenyl) perylene-9-cyano-3,4-dicarboximide, a scattering body based on TiO$_2$ and at least one polymer consisting essentially of polystyrene, polyethylene terephthalate or polycarbonate.

Typically, the concentration of inventive organic fluorescent dye of the formula I is 0.001 to 0.5% by weight, preferably 0.005 to 0.2% by weight, most preferably 0.01 to 0.1% by weight, based in each case on the amount of polymer used. Typically, the concentration of the red organic fluorescent dye is 0.0001 to 0.5% by weight, preferably 0.002 to 0.1% by weight, most preferably 0.005 to 0.05% by weight, based on the amount of the polymer used.

The ratio of at least one inventive organic fluorescent dye to at least one further red organic fluorescent dye is typically in the range from 4:1 to 25:1, preferably 6:1 to 20:1.

In a very particularly preferred embodiment, inventive color converters comprise at least one compound of the formula I as the inventive organic fluorescent dye, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide as the red organic fluorescent dye, scattering bodies based on TiO$_2$, and at least one polymer consisting essentially of polystyrene.

In a very particularly preferred embodiment, inventive color converters comprise at least one compound of the formula I as the inventive organic fluorescent dye, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide as the red organic fluorescent dye, scattering bodies based on TiO$_2$, and at least one polymer consisting essentially of PET.

In a very particularly preferred embodiment, inventive color converters comprise at least one compound of the formula I as the inventive organic fluorescent dye, N,N'-bis(2,6-diisopropylphenyl)-1,7-di(2,6-diisopropylphenoxy)perylene-3,4;9,10-tetracarboximide, N,N'-bis(2,6-diisopropylphenyl)-1,6-di(2,6-diisopropylphenoxy)perylene-3,4;9,10-tetracarboximide as the red organic fluorescent dye, scattering bodies based on TiO$_2$, and at least one polymer consisting essentially of polycarbonate.

If the color converter has a multilayer structure, in one embodiment, one layer comprises at least one red fluorescent dye and another layer at least one inventive fluorescent dye of the formula I or mixtures thereof.

In one embodiment, the at least one red organic fluorescent dye is in the layer of the color converter facing the LED. In another embodiment, the at least one green or green/yellow fluorescent dye is in the layer of the color converter facing the LED.

In a further embodiment, a scattering body is present in the layer facing the LED, above that a color converter and above that in turn optionally a further layer containing a scattering body.

In a preferred embodiment, the color converter has a bilayer structure with a red-fluorescing layer and a green/yellow-fluorescing layer comprising at least one fluorescent dye present in accordance with the invention, with the red dye layer facing the blue light source. In this embodiment, both layers comprise TiO$_2$ as a scattering body.

A further preferred embodiment of color converters has a monolayer structure, with at least one yellow fluorescent dye present in accordance with the invention and at least one red fluorescent dye of formula (IV) and scattering bodies encompassed in one layer. The scattering body is preferably titanium dioxide. In this embodiment, the polymer preferably consists of polystyrene, PET or polycarbonate.

In one embodiment, at least one polymer layer of the color converter has been mechanically reinforced with glass fibers.

Inventive color converters may be in any desired geometric arrangement. The color converters may, for example, be in the form of films, sheets or plaques. Equally, the matrix containing organic fluorescent colorants may be in droplet form or hemispherical form or in the form of lenses with convex and/or concave, flat or spherical surfaces.

"Casting" refers to the embodiment where LEDs or components comprising LEDs are cast or enveloped fully with a polymer comprising organic fluorescent dye.

In one embodiment of the invention, the polymer layers (matrices) comprising organic fluorescent dye are 25 to 250 micrometers thick, preferably 35 to 200 µm and particularly 50 to 160 µm.

In another embodiment, the polymer layers comprising organic fluorescent dye are 0.2 to 5 millimeters thick, preferably 0.3 to 3 mm and more preferably 0.2 to 1 mm.

If the color converters consist of one layer or they have a laminate structure, the individual layers, in a preferred embodiment, are continuous and do not have any holes or interruptions.

The concentration of the organic fluorescent dyes in the polymer is set as a function of the thickness of the color converter and the type of polymer. If a thin polymer layer is used, the concentration of the organic fluorescent dye is generally higher than in the case of a thick polymer layer.

In a preferred embodiment, at least one of the layers or matrices comprising fluorescent dye comprises scattering bodies for light.

In a further preferred embodiment of the multilayer structure, a plurality of layers comprising fluorescent dye and one or more layers comprising scattering bodies without fluorescent dye are present.

Suitable scattering bodies are inorganic white pigments, for example titanium dioxide, barium sulfate, lithopone, zinc oxide, zinc sulfide, calcium carbonate having a mean particle size to DIN 13320 of 0.01 to 10 µm, preferably 0.1 to 1 µm, more preferably 0.15 to 0.4 µm.

Scattering bodies are typically present in an amount of 0.01 to 4.0% by weight, preferably 0.05 to 2% by weight, more preferably 0.1 to 1% by weight, based in each case on the polymer in the layer comprising scattering bodies.

Inventive color converters may optionally comprise further constituents such as a backing layer.

Backing layers serve to impart mechanical stability to the color converter. The type of material for the backing layers is not crucial, provided that it is transparent and has the desired mechanical strength. Suitable materials for backing layers are, for example, glass or transparent rigid organic polymers such as polycarbonate, polystyrene or polymethacrylates or polymethylmethacrylates.

Backing layers generally have a thickness of 0.1 mm to 10 mm, preferably 0.3 mm to 5 mm, more preferably 0.5 mm to 2 mm.

In one embodiment of the invention, inventive color converters have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $Al_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PBT), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH).

A preferred material for barrier layers is glass or a multilayer system composed of alternating layers of $Al_2O_3$ and $SiO_2$ layers.

Preferably, suitable barrier layers have low permeability for oxygen.

More preferably, suitable barrier layers have low permeability for oxygen and water.

Inventive color converters are especially suitable for the conversion of blue light to green/yellow light.

More particularly, they are suitable for conversion of light emitted by blue LEDs. Suitable LEDs are, for example, those based on gallium nitride (GaN) or indium gallium nitride (InGaN). Likewise possible is their use for conversion of light produced by mercury lamps, by organic light-emitting diodes (OLEDs) or by UV LEDs.

Inventive color converters are also especially suitable for the conversion of green or white light to a more red-rich spectrum.

More particularly, they are suitable for conversion of light emitted by green LEDs. Suitable LEDs are, for example, those based on GaInNAs, such as Te-doped GaInNAs and Mg-doped GaInNAs. More particularly, they are suitable for conversion of light emitted by white LEDs to pleasant light with good color rendering.

They are additionally suitable for applications as a light-collecting system (fluorescence collector) in photovoltaics and in fluorescence conversion solar cells.

They are additionally suitable for applications as color converters in displays. These displays are driven with either a blue LED backlight or a white LED backlight or a white OLED light or a blue OLED backlight or a RGB OLED backlight. They contain a photopatternable matrix or a polymeric matrix containing a polymer from the class of acrylates, at least two fluorescent dyes, scattering particles like $TiO_2$ and $ZrO_2$. Also mixtures of fluorescent dyes and inorganic phosphors or quantum dots may be contained.

In a further embodiment, the inventive color converters are used for the conversion of blue light.

In a further embodiment, the color converter is used for conversion of light which has been produced by a blue light emitting diode, using at least one compound of the formula I or mixtures thereof as a fluorescent dye rather than Ce:YAG as a radiation converter. Preferably, the color converter comprises, as fluorescent dye, in addition to the inventive compound of the formula I or mixtures thereof, a red organic fluorescent dye. The red organic fluorescent dye is preferably selected from the compounds of the formulae IV, V and VI. In this embodiment, the blue LED and the color converter are in a remote phosphor arrangement. The color rendering of such an LED meets high demands.

In a further embodiment, the color converter is used for conversion of light which has been produced by a blue light emitting diode, using at least one compound of the formula I or mixtures thereof as a fluorescent dye in combination with at least one inorganic fluorescent colorant selected from rare earth-doped aluminates, silicates, nitrides and garnets, especially cerium-doped yttrium aluminum garnet. In this embodiment, the blue LED and the color converter are in a remote phosphor arrangement.

Inventive color converters on irradiation with light, especially with blue LED light, exhibit a high quantum yield. In addition, they have a high photostability on irradiation with blue light. They have also a high photostability on irradiation with white light Moreover, they are stable toward oxygen and water. They emit pleasant light with good color rendering. A further advantage is that the color converters comprising no rare earths can be provided.

In a further embodiment, the color converter is used for conversion of light which has been produced by a white LED, using at least one compound of the formula I or mixtures thereof as a fluorescent dye. Preferably, the color converter comprises, as fluorescent dye, in addition to the inventive compound of the formula I or mixtures thereof, a red organic fluorescent dye. The red organic fluorescent dye is preferably selected from the compounds of the formulae IV, V and VI. In this embodiment, the white LED and the color converter are in a remote phosphor arrangement. The color rendering of such an LED meets high demands.

Inventive color converters can be produced by different processes.

In one embodiment, the process for producing inventive color converters comprises the dissolution of the at least one polymer and the at least one organic fluorescent dye in a solvent and subsequent removal of the solvent and hotpressing the residual powder into the wished geometric form (platelike or others).

In another embodiment, the process for producing inventive color converters comprises the extrusion of the at least one organic fluorescent dye with the at least one polymer.

The invention further provides lighting devices comprising at least one LED and at least one inventive color converter. The at least one LED is preferably blue and emits light preferably within a wavelength range from 400 to 500 nm, preferably 420 to 480 nm, more preferably 440 to 470 nm, most preferably at 445 to 460 nm.

In one embodiment, inventive lighting devices comprise exactly one LED. In another embodiment, inventive lighting devices comprise two or more LEDs.

In one embodiment, inventive lighting devices comprise a plurality of LEDs, all of which are blue. In another embodiment, inventive lighting devices comprise a plurality of LEDs, at least one LED being blue and at least one LED not being blue but emitting light in another color, for example red.

Furthermore, the type of LED used is not crucial for the inventive lighting devices. In a preferred embodiment, the power density of the LED used is less than 100 mW/cm$^2$, preferably less than 60 mW/cm$^2$. The use of LEDs of higher power densities, such as 150 or 200 mW/cm$^2$, is likewise possible. However, a higher power density of the LED can reduce the lifetime of the fluorescent dyes and the color converters.

Inventive color converters can be used in combination with LEDs in virtually any geometric form and irrespective of the construction of the lighting device.

In one embodiment, color converter and LED are in a phosphor on a chip arrangement.

Preferably, inventive color converters are used in a remote phosphor setup. In this case, the color converter is spatially separated from the LED. In general, the distance between LED and color converter is from 0.1 cm to 50 cm, preferably 0.2 to 10 cm and most preferably 0.5 to 3 cm. Between color converter and LED may be different media such as air, noble gases, nitrogen or other gases or mixtures thereof.

The color converter may, for example, be arranged concentrically around the LED or have a planar geometry or the form of a tube or semitube. It may take the form, for example, of a plaque, sheet or film, be in droplet form or take the form of a casting.

Inventive lighting devices are suitable for lighting in interiors, outdoors, of offices, of vehicles, in torches, games consoles, streetlights, traffic signs.

Inventive lighting devices exhibit a high quantum yield. In addition, they have a long lifetime, especially a high photostability on irradiation with blue light. They emit pleasant light with good color rendering.

The present invention further provides a device producing electric power upon illumination comprising a photovoltaic cell (solar cell) and the color converter as defined above, where at least a part of the incoming light not absorbed by the photovoltaic cell (solar cell) is absorbed by the color converter. The color converter is usually on top of the photovoltaic cell. The color converter is used to modify the spectrum such that UV and visible light are converted to a more bathochromic spectrum that is converted at higher efficiency by the solar cell.

EXAMPLES

Abbreviations used: DCM means dichloromethane; DMF means dimethylformamide; EE means ethyl acetate; FQY means fluorescence quantum yield; HAc means acetic acid; NMP means N-methylpyrrolidone; Rf means retardation factor; Rt means retention time;

I. Preparation of Compound of Formula (I)

Example 1

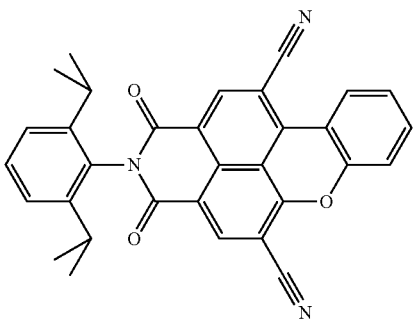 [SMILES: CC(C)c1cccc(C(C)C)c1-n1c(=O)c2cc(C#N)c3oc4ccccc4c4c(C#N)cc(c1=O)c2c34]

A mixture of 0.5 g (0.83 mmol) of 5,11-dibromo-2-(2,6-diidopropylphenyl)-1H-xantheno[2,1,9-def]isoquinoline-1,3(2H)-dione (prepared as described in WO 2014/131628, example compound 2404) in 20 mL of N-methylpyrrolidone (NMP) and 0.179 g (2 mmol) of CuCN were heated to 170° C. After 2 hours, further 0.1 g of CuCN were added and after 3 further hours, further 0.1 g of CuCN were added. The reaction mixture was cooled after admixed with water, filtered, and washed with methanol. The residue was chromatographed with toluene/ethyl acetate (20:1) on silica gel. This gave 250 mg (61%) of the title compound. Rf: 0.56.

Absorption: $\lambda_{max}$ (CH$_2$Cl$_2$): 427; emission: $\lambda_{max}$ (CH$_2$Cl$_2$): 497 nm; FQY (CH$_2$Cl$_2$) 100%

Example 2

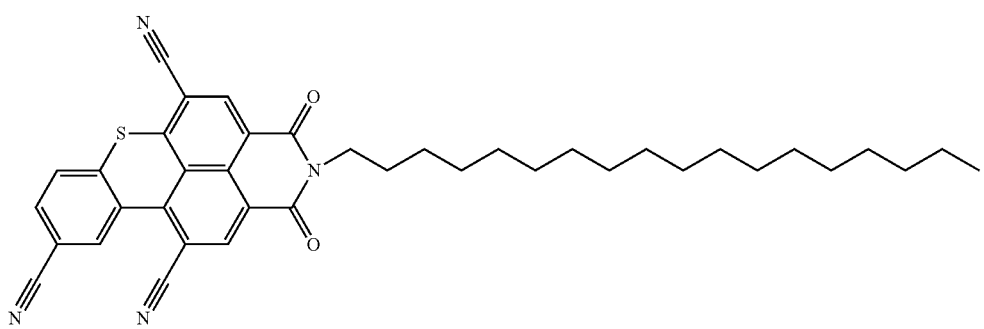 [SMILES: CCCCCCCCCCCCCCCCCCn1c(=O)c2cc(C#N)c3sc4ccc(C#N)cc4c4c(C#N)cc(c1=O)c2c34]

2.1 Preparation of

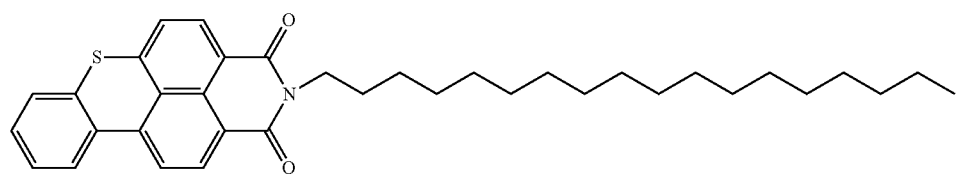 [SMILES: CCCCCCCCCCCCCCCCCCn1c(=O)c2ccc3sc4ccccc4c4ccc(c1=O)c2c34]

The title compound was prepared according to Guttsait, A. V.; Balodis, K. A.; Meirovits, I. A. Chemistry of Heterocyclic Compounds (New York, N.Y., United States), 1993, vol. 29, No. 10 p. 1226-1229.

2.2 Preparation of

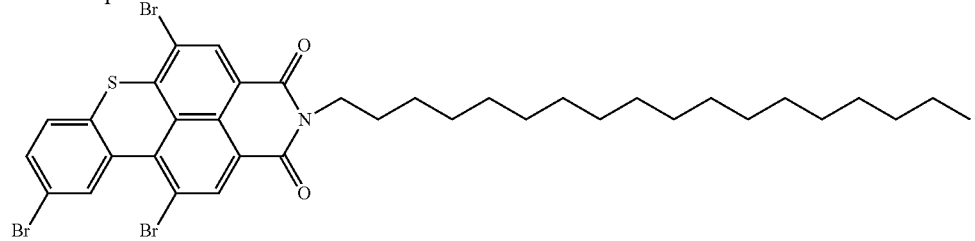 [SMILES: CCCCCCCCCCCCCCCCCCn1c(=O)c2cc(Br)c3sc4ccc(Br)cc4c4c(Br)cc(c1=O)c2c34]

A mixture of 56 mL of chlorobenzene, 40 mL of water, 5.0 g (9 mmol) of the compound of example 2.1 and 45.2 g (285 mmol) of bromine were reacted at 35° C. for 16 hours. Bromine was blown out with nitrogen and the product was precipitated with ethanol, filtered and washed with water. The title product was obtained in quantitative yield (6.7 g). Rf=0.72 (toluene)

2.3 Preparation of

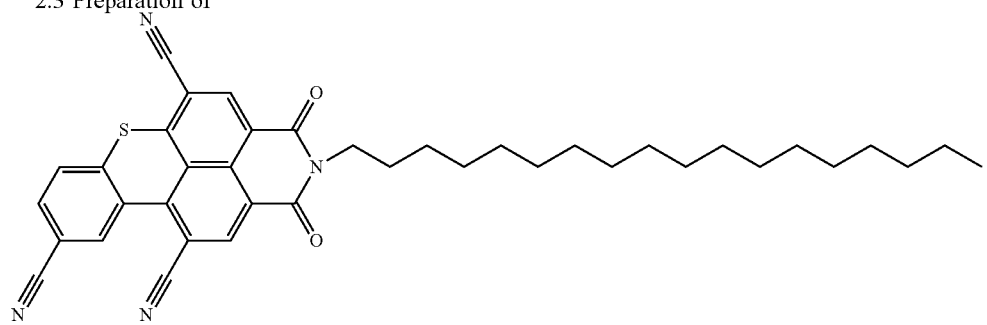

A mixture of 1.0 g of the compound of example 2.2, 34 mL of NMP and 0.627 g of CuCN were heated to 160° C. After 1 hour further 0.2 g of CuCN were added. One hour later further 0.2 g of CuCN were added and the reaction was heated for 16 hours. The product was precipitated by the addition of water, filtered and dried. The crude product was purified by column chromatography (SiO$_2$). Rf=0.22 (toluene).

Absorption: $\lambda_{max}$ (CH$_2$Cl$_2$): 455 nm; emission: $\lambda_{max}$ (CH$_2$Cl$_2$): 511 nm; FQY (CH$_2$Cl$_2$): 100%

Example 3

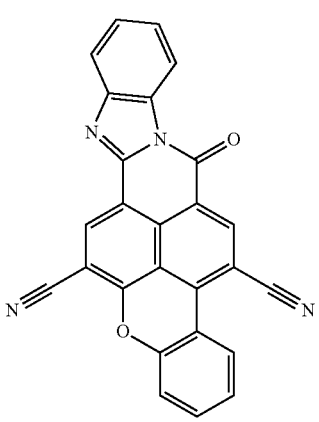

-continued

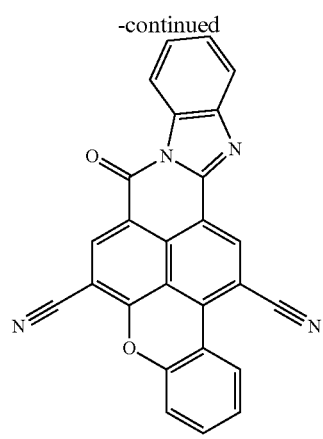

3.1 Preparation of

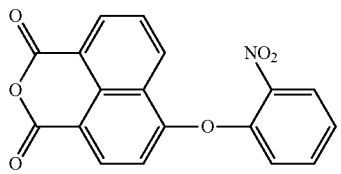 [SMILES: O=C1OC(=O)c2ccc(Oc3ccccc3[N+](=O)[O-])c3cccc1c23]

A mixture of 400 mL of NMP, 15 g (54.14 mmol) of 4-bromo-1,8-naphthalic anhydride, 19.98 g (140.76 mmol)

of 2-nitrophenol, 7.15 g of KOH (108.28 mmol) and 0.24 g (3.79 mmol) of Cu powder was stirred at 130° C. for 21 hours. After cooling to room temperature, the mixture was poured onto diluted sulfuric acid. The precipitate was filtered off and vacuum dried at 70° C. The solid was stirred in acetone, dissolved in DCM, filtered and vacuum dried at 70° C. to give 11.72 g (34.96 mmol, 64.6%) of a beige solid.

Rf (toluene/EE/HAc 10/2/1)=0.51. Purity: 91.4% (HPLC (254 nm)). m/z=336.0 (M+H) $R_t$=1.111 min (LCMS, ESI).

3.2 Preparation of

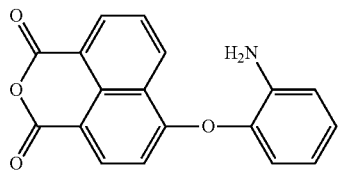 [SMILES: Nc1ccccc1Oc1ccc2c3c(cccc13)C(=O)OC2=O]

To a mixture of 450 mL of DMF, 5.72 g (17.06 mmol) of the compound from example 3.1 and 0.91 g (0.85 mmol) of 10% Pd/C were added 1.15 L of hydrogen at room temperature for 21 hours. The mixture was then filtered and poured onto 2 L of an aqueous solution of 20% by weight NaCl. The crude solid was washed with water and vacuum dried at 70° C. to give 4.17 g (13.66 mmol, 80.1%) of a bright yellow solid. Rf (DCM/EE 9/1)=0.84. Purity: 93.0% (HPLC (254 nm)); m/z=306.0 (M+H) Rt=1.051 min (LCMS, ESI).

3.3 Preparation of

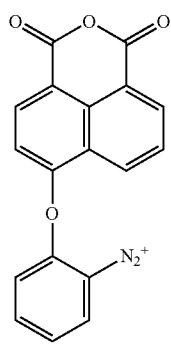

A mixture of 340 mL of acetic acid, 35 mL of concentrated HCl, 70 mL of H$_2$O, 6.85 g (22.44 mmol) of the compound from example 3.2 and 1.70 g (24.68 mmol) of sodium nitrite was stirred at 0° C. for 2 hours. The reaction mixture was used without further purification in the next step.

3.4 Preparation of

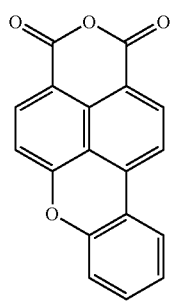

A mixture of 550 mL of H$_2$O, 35 mL of acetic acid and 13.67 g (54.75 mmol) of copper(II) sulfate pentahydrate was refluxed. The reaction mixture from example 3.3 was added and the mixture was refluxed for 1 hour. After cooling, water was added, the precipitate was filtered off and vacuum dried at 70° C. The resulting solid was recrystallized (DMF) to give 2.04 g (7.08 mmol, 31.5%) of a yellow solid.

Rf (toluene/EE 10/1)=0.58; Purity 92.0% (HPLC (254 nm)).

3.5 Preparation of

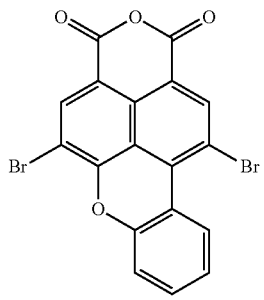 [SMILES: O=c1oc(=O)c2cc(Br)c3c4ccccc4oc4c(Br)cc1c2c43]

A mixture of 7.8 mL of chlorobenzene, 4.6 mL of water, 600 mg (2.08 mmol) of the compound of example 3.4 and 3.35 mL (65.60 mmol) of bromine was stirred at 35° C. for 20 hours. The reaction mixture was concentrated; the remainder was partitioned between DCM and aqueous sodium thiosulfate solution. The organic phase was dried and the solvent evaporated to give a yellow solid (1.03 g (2.08 mmol, 99.8%) (mixture of the title compound and the monobromine compound).

Rf (toluene/EE 10/1)=0.73; m/z=445.9 (M+H); Rt=4.909 min (HPLC-MS, APCI).

3.6 Preparation of

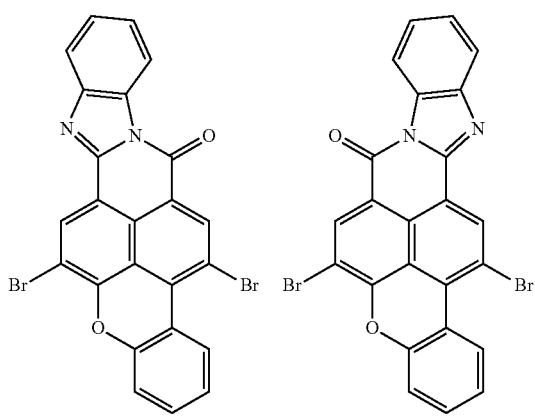

A mixture of 12 mL of quinoline, 1.03 g (2.32 mmol) of the compound of example 3.5, 0.25 g (2.32 mmol) of 1,2-phenylendiamine and 0.21 g (1.16 mmol) of zinc acetate was stirred at 135° C. for 3 hours. After cooling, the precipitate was filtered off and vacuum dried at 70° C. to give 0.81 g (1.56 mmol, 67.3%) of the title compound.

Rf (toluene/EE 10/1)=0.62 and 0.64; m/z=519 (M+H); Rt=6.732 min and 6.861 min (HPLC-MS, APCI).

3.7 Preparation of

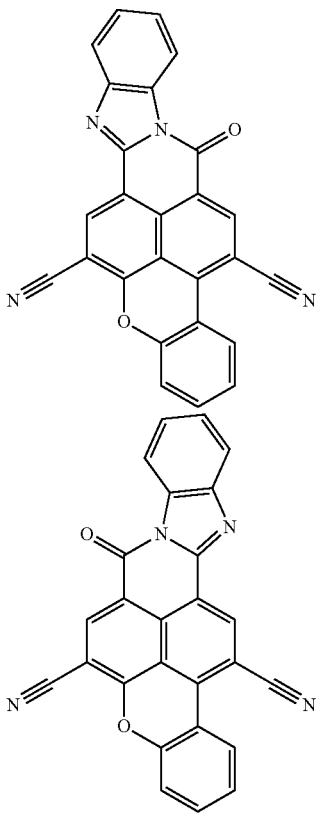

A mixture of 30 mL NMP, 0.8 g (1.54 mmol) of the compounds from preparation 3.6 and 0.72 g (8.02 mmol) was stirred at 170° C. for 65 hours. The mixture was cooled and poured onto water. The solid was filtered off and vacuum dried at 70° C. The crude product was purified by column chromatography (DCM/methanol 1-10%) to give 3.4 mg (0.01 mmol, 0.5%) of the title compounds.

Rf (toluene/ethyl acetate 10/1)=0.43; m/z=411 (M+H) (MALDI).

Example 4

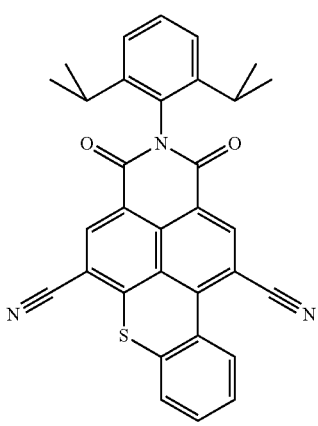 [SMILES: CC(C)c1cccc(C(C)C)c1-n1c(=O)c2cc(C#N)c3sc4ccccc4c4c(C#N)cc(c1=O)c2c34]

4.1 Preparation of

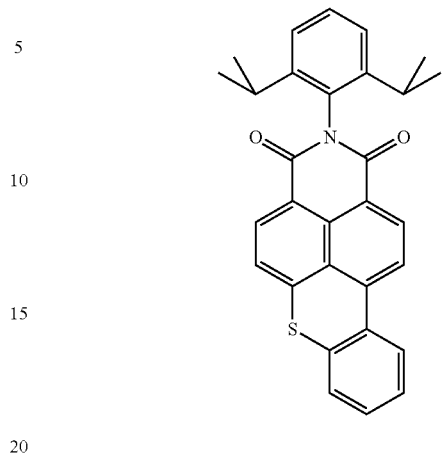

A mixture of 50 mL of NMP, 1.6 g (5 mmol) of benzo[k,l]thioxanthene dicarboxylic anhydride, 2.8 g (15 mmol) of diisopropylaniline and 1.8 g (10 mmol) of zinc acetate was stirred at 200° C. for 20 hours. After cooling to room temperature, 500 mL of diluted hydrochloric acid were added. The precipitate formed was sucked off and vacuum dried at 70° C. to 1.89 g (82%) of the title compound as yellow-brown solid.

Rf (toluole:EE 10:1)=0.51.

4.2 Preparation of

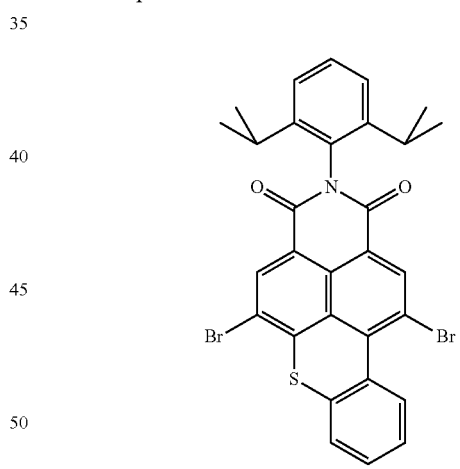

A mixture of 1.62 g (3.5 mmol) of the compound of example 4.1, 100 mL of trichloromethane, 5.6 g (35 mmol) of bromine was heated at 60° C. for 4 hours. Then further 5.6 g (35 mmol) of bromine were added and the reaction mixture was refluxed for 6 hours. After cooling to room temperature, the reaction mixture was poured onto 500 mL of diluted aqueous sodium hydroxide solution, stirred for 10 minutes and extracted with DCM. The combined organic phases were dried and the solvent was evaporated in vacuum to give 2.44 g (quant.) of a yellow crude product. Rf (Toluene/EE 50:1)=0.44.

4.3 Preparation of

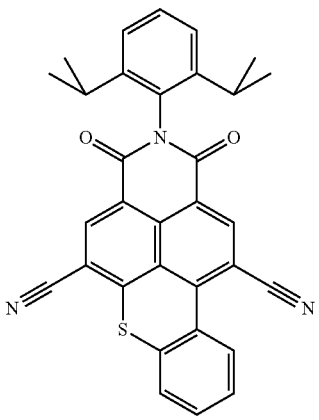 [SMILES: CC(C)c1cccc(C(C)C)c1-n1c(=O)c2cc(C#N)c3sc4ccccc4c4c(C#N)cc(c1=O)c2c34]

A mixture of 50 mL of NMP, 2.17 g of the compound of example 4.2 and 0.94 g of CuCN were heated at 170° C. for 7 hours. The reaction was cooled to room temperature and poured onto 500 mL of aqueous sodium chloride solution. The precipitate was filtered off and vacuum dried at 70° C. to give 1.55 g (86%) of a yellow solid. The crude product was purified by chromatography (toluene, toluene/EE 50:1). This product was further purified by recrystallization from toluene to give 420 mg of the title compound as yellow solid. Rf (toluene:EE 50:1)=0.18. Absorption: λmax (CH$_2$Cl$_2$): 486 nm.

Example 5

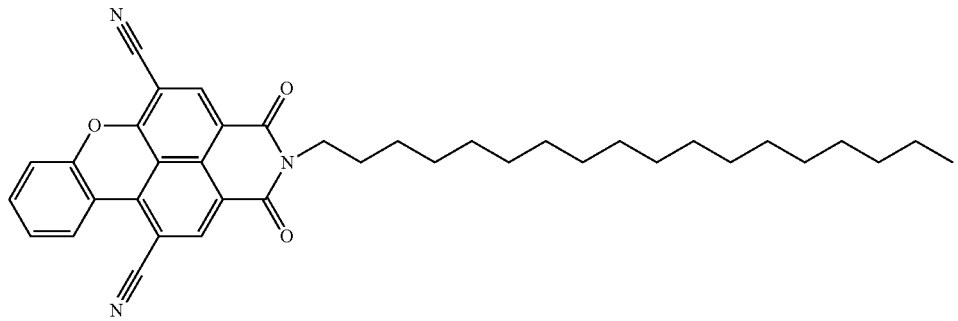 [SMILES: CCCCCCCCCCCCCCCCCCn1c(=O)c2cc(C#N)c3oc4ccccc4c4c(C#N)cc(c1=O)c2c34]

5.1 Preparation of

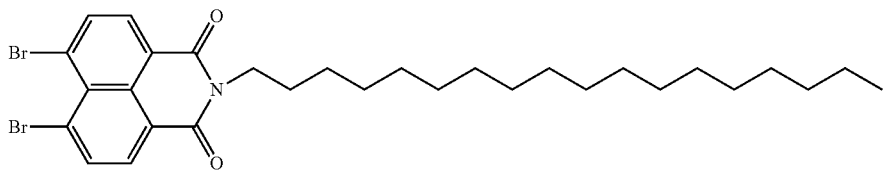 [SMILES: CCCCCCCCCCCCCCCCCCN1C(=O)c2ccc(Br)c3c(Br)ccc(c23)C1=O]

A mixture of 100 mL of toluene, 100 mL of ethanol, 5 g (14.05 mmol) 4,5-dibromo-1,8-naphthalic anhydride and 7.57 g (28.10 mmol) of octadecylamine was refluxed for 1.5 hours. After cooling, the precipitate was filtered off and vacuum dried at 70° C. to give 6.58 g (9.48 mmol, 87.45%) of a solid.

Rf (Cyclohexane/DCM ½)=0.48. Purity: 87.5% (HPLC, 254 nm). m/z=607. Rt=15.134 min (HPLC-MS, APCl).

5.2 Preparation of

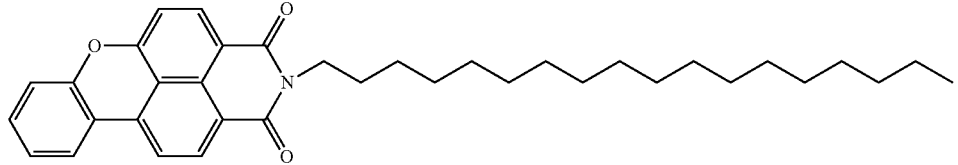 [SMILES: CCCCCCCCCCCCCCCCCCn1c(=O)c2ccc3oc4ccccc4c4ccc(c1=O)c2c34]

A mixture of 1.14 g (1.64 mmol) of the compound of example 5.1, 468 mg (3.28 mmol) of 2-hydroxyphenylboronic acid, 2 mL of water, 15 mL of methoxybenzene, 455 mg (3.2 mmol) of potassium carbonate, 728 mg of polystyrene-supported tetrakis(triphenylphosphine)palladium (0.11 mmol/g; (0,082 mmol) from Biotage) was warmed to 80° C. After 75 minutes, further 100 mg (0.7 mmol) of 2-hydroxypheny-Iboronic acid and after all 115 minutes, further 100 mg (0.7 mmol) of 2-hydroxyphenylboronic acid were added. After cooling to room temperature, the catalyst was removed and the remainder washed with DCM. Organic phases were concentrated and the remainder was purified by chromatography (cyclohexane/DCM 20-60%). The title compound was further washed with methanol to give 785 mg (1.45 mmol, 88.3%) of a yellow solid. Rf (Cyclohexane/DCM ½)=0.19.

5.3 Preparation of

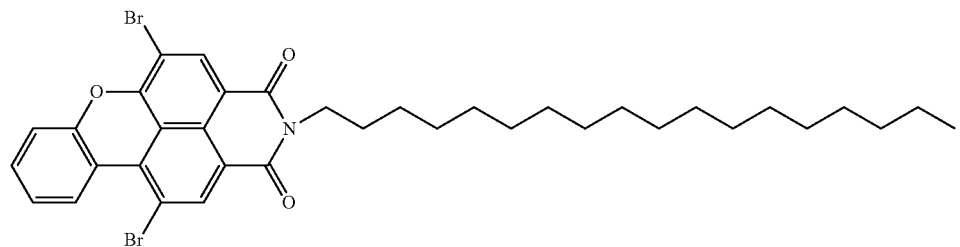 [SMILES: CCCCCCCCCCCCCCCCCCn1c(=O)c2cc(Br)c3oc4ccccc4c4c(Br)cc(c1=O)c2c34]

A mixture of 2.58 g (4.78 mmol) of the compound of example 5.2, 200 mL of trichloromethane and 2.5 ml (7.8 g; 48.8 mol) of bromine was refluxed for 5 days. Then, bromine and trichloromethane were distilled off. The yellow remainder was washed with diluted aqueous NaHSO₃ solution, washed with water and vacuum dried to give 3.34 g (84%) of the yellow title compound. Rf (toluene/EE=10:1)=0.7.

5.4 Preparation of

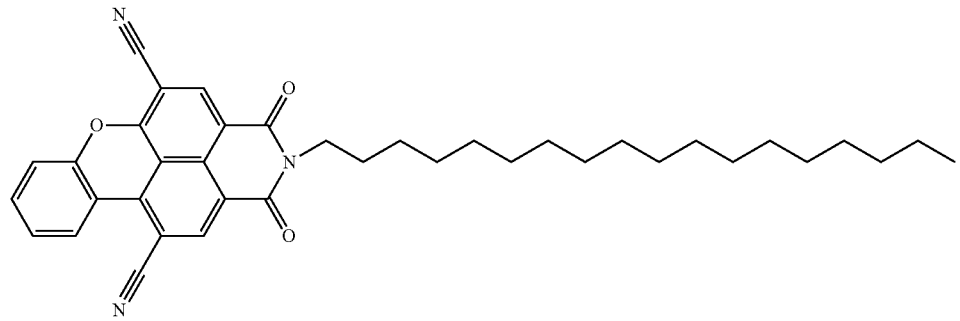 [SMILES: CCCCCCCCCCCCCCCCCCn1c(=O)c2cc(C#N)c3oc4ccccc4c4c(C#N)cc(c1=O)c2c34]

To 3.56 g (4.90 mmol) of the compound of example 5.3 was dissolved in 150 mL of NMP were added 1.316 g (14.691 mmol) of CuCN. The reaction mixture was heated at 170° C. for 3 days under stirring. After cooling to room temperature, the precipitate was filtered of, washed with water and methanol and purified by column chromatography on SiO₂. Recrystallization from toluene gave 2.28 g (80%) of the title compound as yellow solid. Rf (toluene/EE 10:1)=0.55.

Example 6

6.1 Preparation of

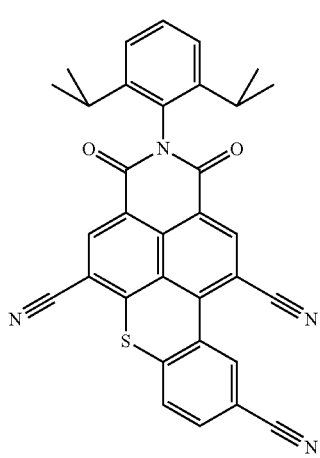 [SMILES: CC(C)c1cccc(C(C)C)c1-n1c(=O)c2cc(C#N)c3sc4ccc(C#N)cc4c4c(C#N)cc(c1=O)c2c34]

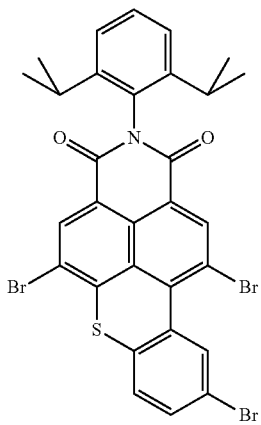 [SMILES: CC(C)c1cccc(C(C)C)c1-n1c(=O)c2cc(Br)c3sc4ccc(Br)cc4c4c(Br)cc(c1=O)c2c34]

To a solution of 11.13 g (24 mmol) of the compound of example 4.1 in 50 mL of dichlorobenzene, 36 mL of water and 38.4 g of bromine (240 mmol) were added. Then further 25 mL of dichlorobenzene and 18 mL of water were added. The reaction mixture was warmed to 40° C. for 3 hours and then cooled to room temperature. The reaction mixture was poured onto 500 mL of methanol. The reaction mixture was filtered, the remainder was washed with methanol and vacuum dried. Purification by column chromatography with toluene/EE (10:1) gave 4.8 g (30%) of the title compound. Rf (toluene)=0.36.

6.2 Preparation of

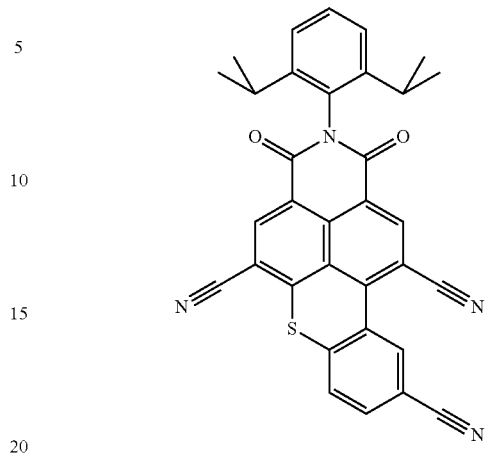

To a solution of 1.4 g (2 mmol) of the compound of example 6.1 in 30 mL of NMP were added 0.72 g of CuCN (8 mmol). After heating to 170° C. for 4 hours, further 0.72 g of CuCN were added and the mixture was heated at 170° C. for further 6 hours. Further 0.72 g of CuCN were added and heated at 170° C. for further 16 hours. After cooling to room temperature, the reaction mixture was poured onto 500 mL of sodium chloride solution and diluted aqueous hydrochloride acid was added. The precipitate is filtered off, washed with water and vacuum dried to give 1.88 g of a crude product which was purified by chromatography (toluene). Yield: 818 mg (80%) of an orange solid.

Rf (toluene/EE 10:1)=0.49. Absorption: $\lambda_{max}$ ($CH_2Cl_{12}$): 457 nm; emission $\lambda_{max}$ ($CH_2Cl_2$): 514 nm; FQY ($CH_2Cl_2$): 98.1%.

II. Preparation of Color Converters
Production of the Color Converters for Testing of the Dyes:

The fluorescent dyes produced according to the examples were used to produce color converters. For this purpose, these were incorporated as described hereinafter into a matrix composed of a polymer. The polymer used was PMMA (Plexiglas® 6N from Evonik), polystyrene (PS168 N from BASF) and PC (Macrolon® 2808 from Bayer).

About 2.5 g of polymer and 0.02% by weight of the dye was dissolved in about 5 mL of methylene chloride, and 0.5% by weight of $TiO_2$ (Kronos 2220) was dispersed therein, based in each case on the amount of polymer used. The solution/dispersion obtained was coated onto a glass surface using an applicator frame (wet film thickness 400 µm). After the solvent had dried off, the film was detached from the glass and dried in a vacuum drying cabinet at 50° C. overnight. Two circular film pieces having a diameter of 15 mm were punched out of each film of thickness 80 to 85 µm, and these served as analysis samples.

Fluorescence quantum yields (FQY) of the analysis samples were measured with the C9920-02 quantum yield measuring system (from Hamamatsu). This was done by illuminating each of the samples with light of 445 to 455 nm in an integration sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities over the spectrum of the unabsorbed excitation light or over that of the emitted fluorescent light gives the degree of absorption or fluorescence intensity or fluorescence quantum yield of each sample.

Results of Fluorescent Quantum Yield Measurements:

Compound of example 1:
PS-film: Emission $\lambda_{max}$: 495 nm; FQY: 92%.
PC-film: Emission $\lambda_{max}$: 495 nm; FQY: 92%.

Compound of example 2:
PS-film: Emission $\lambda_{max}$: 511.5 nm; FQY: 82%.
PC-film: Emission $\lambda_{max}$: 514 nm; FQY: 82%.

Compound of example 3:
PC-film: Emission $\lambda_{max}$: 535 nm; FQY: 77%.

Compound of example 4:
PS-film: Emission $\lambda_{max}$: 521 nm; FQY: 87%.
PC-film: Emission $\lambda_{max}$: 525 nm; FQY: 85%.

Compound of example 6:
PS-film: Emission $\lambda_{max}$: 512 nm; FQY: 83.4%.
PC-film: Emission $\lambda_{max}$: 516 nm; FQY: 83%.

Comparative compound 2401 from WO 2014/131628:
PS-film: Emission $\lambda_{max}$: 511 nm; FQY: 92%.
PC-film: Emission $\lambda_{max}$: 495 nm; FQY: 93%.

The lifetimes of the compounds of examples 1, 2, 3 and 4 and of a comparative compound (compound 2401 from WO 2014/131628) in a PS- and PC-film are evaluated by the irradiation time until the fluorescence intensity reaches 80% (T80) of its initial value. To this end, polymer-films doped with TiO$_2$ and fluorescent dye were prepared as described above. The results are summarized in table I.

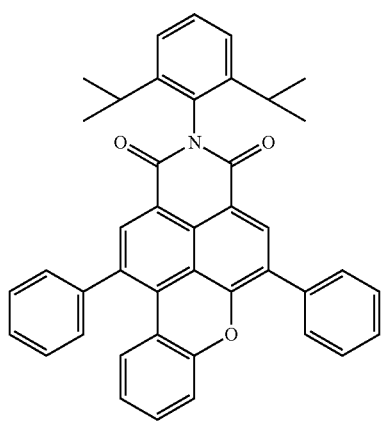 [SMILES: CC(C)c1cccc(C(C)C)c1-n1c(=O)c2cc(-c3ccccc3)c3oc4ccccc4c4c(-c5ccccc5)cc(c1=O)c2c34]

Comparative compound: Compound 2401 from WO 2014/131628

TABLE I

| Lifetime (days) upon irradiation (T80) | | |
| --- | --- | --- |
| Compound | T80 (PS-film) | T80 (PC-film) |
| Compound of example 1 | 10.8 days | 18.6 days |
| Compound of example 2 | — | 11.2 days |
| Compound of example 3 | — | 22.4 days |
| Compound of example 4 | — | 17.2 days |
| Compound 2401 from WO 2014/131628 | 5.9 days | 5.6 days |

As can be seen from table I, the compounds according to the present invention have a substantial longer lifetime under the irradiation conditions than a structurally similar non-cyanated compound known from prior art.

The invention claimed is:

1. A cyanated compound of formula (I):

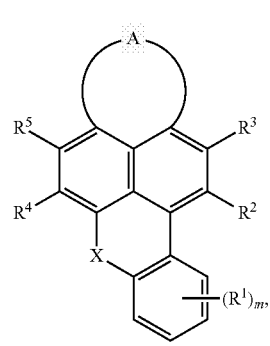

(I)

wherein:
m is 0, 1, 2, 3 or 4;
each $R^1$ independently from each other is bromine, chlorine, cyano, a $C_1$-$C_{24}$-alkyl, a $C_1$-$C_{24}$-haloalkyl, a $C_1$-$C_{24}$-alkoxy, a $C_1$-$C_{24}$-haloalkoxy, a $C_3$-$C_{24}$-cycloalkyl, a heterocycloalkyl, a heteroaryl, a $C_6$-$C_{24}$-aryl, a $C_6$-$C_{24}$-aryloxy, or a $C_6$-$C_{24}$-aryl-$C_1$-$C_{10}$-alkylene, where rings of cycloalkyl, heterocycloalkyl, heteroaryl, aryl, aryloxy and-aryl-alkylene are unsubstituted or substituted with 1, 2, 3, 4 or 5 identical or different radicals $R^{1a}$ and where $C_1$-$C_{24}$-alkyl, $C_1$-$C_{24}$-haloalkyl, $C_1$-$C_{24}$-alkoxy, and the alkylene moiety of the $C_6$-$C_{24}$-aryl-$C_1$-$C_{10}$-alkylene are optionally interrupted by at least one of O, S or $NR^c$;
at least one of the radicals $R^2$, $R^3$, $R^4$ and $R^5$ is CN, and remaining radicals, independently from each other, are hydrogen, chlorine or bromine;
X is O, S, SO or SO$_2$;
A is a diradical of formulae (A.1), (A.2), (A.3), or (A.4);

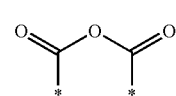

(A.1)

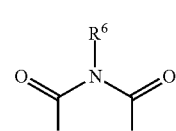

(A.2)

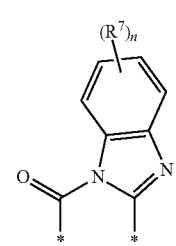

(A.3)

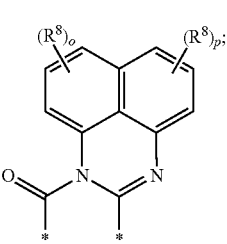

(A.4)

* in each case denotes the point of attachments to the remainder of the molecule;

n is 0, 1, 2, 3 or 4;
o is 0, 1, 2 or 3;
p is 0, 1, 2 or 3;
$R^6$ is hydrogen, a $C_1$-$C_{24}$-alkyl, a $C_1$-$C_{24}$-haloalkyl, a $C_3$-$C_{24}$-cycloalkyl, a $C_6$-$C_{24}$-aryl or a $C_6$-$C_{24}$-aryl-$C_1$-$C_{10}$-alkylene, where rings of cycloalkyl, aryl, and aryl-alkylene are unsubstituted or substituted with 1, 2, 3, 4 or 5 identical or different radicals $R^{6a}$, and where $C_1$-$C_{24}$-alkyl, $C_1$-$C_{24}$-haloalkyl and the alkylene moiety of the $C_6$-$C_{24}$-aryl-$C_1$-$C_{10}$-alkylene are optionally interrupted by one or more heteroatoms or heteroatomic groups of O, S and $NR^c$;
each $R^7$ independently from each other is bromine, chlorine, cyano, —$NR^aR^b$, a $C_1$-$C_{24}$-alkyl, a $C_1$-$C_{24}$-haloalkyl, a $C_1$-$C_{24}$-alkoxy, a $C_1$-$C_{24}$-haloalkoxy, a $C_3$-$C_{24}$-cycloalkyl, a heterocycloalkyl, a heteroaryl, a $C_6$-$C_{24}$-aryl, a $C_6$-$C_{24}$-aryloxy, or a $C_6$-$C_{24}$-aryl-$C_1$-$C_{10}$-alkylene, where rings of cycloalkyl, heterocycloalkyl, heteroaryl, aryl and aryl-alkylene are unsubstituted or substituted with 1, 2, 3, 4 or 5 identical or different radicals $R^{7a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of the $C_6$-$C_{24}$-aryl-$C_1$-$C_{10}$-alkylene are optionally interrupted by at least one of O, S and $NR^c$;
each $R^8$ independently from each other is bromine, chlorine, cyano, $NR^aR^b$, a $C_1$-$C_{24}$-alkyl, a $C_1$-$C_{24}$-haloalkyl, a $C_1$-$C_{24}$-alkoxy, a $C_1$-$C_{24}$-haloalkoxy, a $C_3$-$C_{24}$-cycloalkyl, a heterocycloalkyl, a heteroaryl, a $C_6$-$C_{24}$-aryl, a $C_6$-$C_{24}$-aryloxy, or a $C_6$-$C_{24}$-aryl-$C_1$-$C_{10}$-alkylene, where rings of cycloalkyl, heterocycloalkyl, heteroaryl, aryl and aryl-alkylene are unsubstituted or substituted with 1, 2, 3, 4 or 5 identical or different radicals $R^{8a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of the $C_6$-$C_{24}$-aryl-$C_1$-$C_{10}$-alkylene are optionally interrupted by at least one of O, S and $NR^c$;
each $R^9$ independently from each other is bromine, chlorine, cyano, $NR^aR^b$, a $C_1$-$C_{24}$-alkyl, a $C_1$-$C_{24}$-haloalkyl, a $C_1$-$C_{24}$-alkoxy, a $C_1$-$C_{24}$-haloalkoxy, a $C_3$-$C_{24}$-cycloalkyl, a heterocycloalkyl, a heteroaryl, a $C_6$-$C_{24}$-aryl, a $C_6$-$C_{24}$-aryloxy, or a $C_6$-$C_{24}$-aryl-$C_1$-$C_{10}$-alkylene, where rings of cycloalkyl, heterocycloalkyl, heteroaryl, aryl and aryl-alkylene are unsubstituted or substituted with 1, 2, 3, 4 or 5 identical or different radicals $R^{9a}$ and where $C_1$-$C_{24}$-alkyl, $C_1$-$C_{24}$-haloalkyl, $C_1$-$C_{24}$-alkoxy, $C_1$-$C_{24}$-haloalkoxy and the alkylene moiety of the $C_6$-$C_{24}$-aryl-$C_1$-$C_{10}$-alkylene are optionally interrupted by at least one of O, S and $NR^c$;
$R^{1a}$, $R^{6a}$, $R^{7a}$, $R^{8a}$, $R^{9a}$ are independently of one another a $C_1$-$C_{24}$-alkyl, a $C_1$-$C_{24}$-fluoroalkyl, a $C_1$-$C_{24}$-alkoxy, fluorine, chlorine or bromine;
$R^a$, $R^b$, $R^c$ are independently of one another hydrogen, a $C_1$-$C_{20}$-alkyl, a $C_3$-$C_{24}$-cycloalkyl, a heterocycloalkyl, a hetaryl or a $C_6$-$C_{24}$-aryl.

2. The cyanated compound of formula (I) according to claim 1, wherein X is O or S.

3. The cyanated compound of formula (I) according to claim 1, wherein $R^2$ and $R^4$ are each cyano, and $R^3$ and $R^5$ are each hydrogen.

4. The cyanated compound of formula (I) according to claim 1, wherein A is a radical of the formula (A.2).

5. The cyanated compound of formula (I) according to claim 4, wherein:
$R^6$ is selected from the group consisting of a linear $C_1$-$C_{24}$-alkyl, a radical of the formula (B.1) and a radical of the formula (B.2):

(B.1)

(B.2)

# represents the bonding site to the nitrogen atom;
$R^d$ and $R^e$, in the formula (B.1), independently from each other are a $C_1$-$C_{23}$-alkyl, where the sum of the carbon atoms of the $R^d$ and $R^e$ radicals is an integer from 2 to 23; and
$R^f$, $R^g$ and $R^h$, in the formula (B.2) are independently a $C_1$- to $C_{20}$-alkyl, where the sum of the carbon atoms of the $R^f$, $R^g$ and $R^h$ radicals is an integer from 3 to 23.

6. The cyanated compound of formula (I) according to claim 4, in which $R^6$ is selected from the group consisting of a radical of the formula (C.1), a radical of the formula (C.2) and a radical of the formula (C.3):

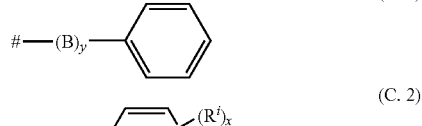
(C.1)

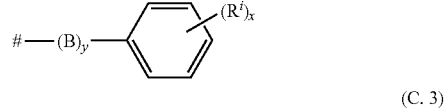
(C.2)

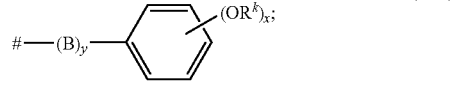
(C.3)

# represents the bonding side to the nitrogen atom;
B where present, is a $C_1$-$C_{10}$-alkylene group optionally interrupted by one or more nonadjacent groups selected from —O— and —S—;
y is 0 or 1;
$R^i$ is independently of one another a $C_1$-$C_{24}$-alkyl, a $C_1$-$C_{24}$-fluoroalkyl, fluorine, chlorine or bromine;
$R^k$ is independently a $C_1$-$C_{24}$-alkyl;
x in formulae C.2 and C.3 is 1, 2, 3,4 or 5.

7. The cyanated compound according to claim 1, wherein m is zero or one.

8. A color converter, comprising at least one polymer as a matrix and at least one cyanated compound of claim 1 or a mixture thereof as a fluorescent dye,
wherein the at least one polymer comprises a polystyrene, a polycarbonate, a polymethylmethacrylate, a polyvinylpyrrolidone, a polymethacrylate, a polyvinyl acetate, a polyvinyl chloride, a polybutene, a silicone, a polyacrylate, an epoxy resin, a polyvinyl alcohol, a poly(ethylene vinylalcohol)-copolymer (EVA, EVOH), a polyacrylonitrile, a polyvinylidene chloride (PVDC), a polystyreneacrylonitrile (SAN), a polybutylene terephthalate (PBT), a polyethylene terephthalate (PET), a polyvinyl butyrate (PVB), a polyvinyl chloride (PVC), a polyamide, a polyoxymethylene, a polyimide, a polyetherimide or mixtures thereof.

9. The color converter according to claim 8, further comprising at least one inorganic white pigment as a scattering body.

10. The color converter according to claim 8, further comprising at least one fluorescent dye of formulae (IV), (V) or (VI):

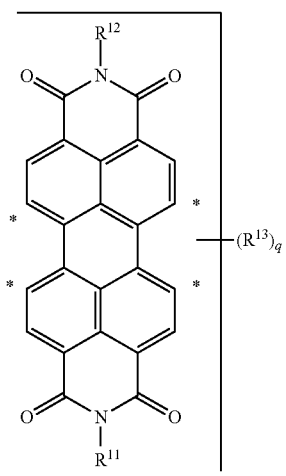

(IV)

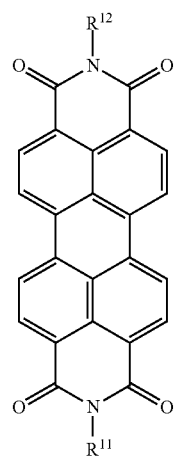

(V)

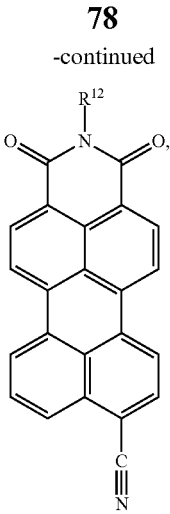

(VI)

wherein:

q is 1 to 4, $R^{11}$, $R^{12}$ are each independently a $C_1$-$C_{30}$-alkyl, a $C_3$-$C_8$-cycloalkyl, an aryl, a hetaryl, or an aryl-$C_1$-$C_{10}$-alkylene, where aromatic rings are unsubstituted or mono- or polysubstituted by a $C_1$-$C_{10}$-alkyl;

$R^{13}$ is aryloxy which is unsubstituted or mono- or polysubstituted by halogen, a $C_1$-$C_{10}$-alkyl or a $C_6$-$C_{10}$-aryl, where $R^{13}$ radicals are at one or more of the positions indicated by *.

11. The color converter according to claim 10, wherein the at least one organic fluorescent dye is selected from the group consisting of N,N'-bis(2,6-diisopropylphenyl)-1,6,7,12-tetraphenoxyperylene-3,4;9,10-tetracarboximide, N,N'-bis(2,6-diisopropylphenyl)-1,7-di(2,6-diisopropylphenoxy) perylene-3,4;9,10-tetracarboximide, N,N'-bis(2,6-diisopropylphenyl)-1,6-di(2,6-diisopropylphenoxy) perylene-3,4;9,10-tetracarboximide, N,N'-bis(2,6-diisopropylphenyl)-1,7-di(p-tert-octylphenoxy)perylene-3,4;9,10-tetracarboximide, N,N'-bis(2,6-diisopropylphenyl)-1,6-di(p-tert-octylphenoxy)perylene-3,4;9,10-tetracarboximide, N,N'-bis(2,6-diisopropylphenyl)-1,7-diphenoxyperylene-3,4;9,10-tetracarboximide, N,N'-bis(2,6-diisopropylphenyl)-1,6-diphenoxyperylene-3,4;9,10-tetracarboximide, N,N'-bis(2,6-diisopropylphenyl)-1,7-di(2,6-diphenyllphenoxy)perylene-3,4;9,10-tetracarboximide, N,N'-bis(2,6-diisopropylphenyl)-1,6-di(2,6-diphenylphenoxy)perylene-3,4;9,10-tetracarboximide and mixtures thereof.

12. A process, comprising converting light generated by an LED with the color converter of claim 8.

13. A display, comprising the color converter of claim 8.

14. A lighting device, comprising at least one LED and at least one color converter of claim 8.

15. A device producing electric power upon illumination, the device comprising a photovoltaic cell and the color converter of claim 8, wherein at least a part of light not absorbed by the photovoltaic cell is absorbed by the color converter.

16. The cyanated compound of formula (I) according to claim 1, wherein $R^1$ is selected from the group consisting of cyano, bromine, unsubstituted phenyl or phenyl substituted with 1 or 2 radicals selected from $C_1$-$C_4$-alkyl.

* * * * *